(12) United States Patent
Ericson

(10) Patent No.: US 8,999,376 B2
(45) Date of Patent: Apr. 7, 2015

(54) TISSUE PATCH

(71) Applicant: Xcede Technologies, Inc., Rochester, MN (US)

(72) Inventor: Daniel Grant Ericson, Rochester, MN (US)

(73) Assignee: Xcede Technologies, Inc., Rochester, MN (US)

( * ) Notice: Subject to any disclaimer, the term of this patent is extended or adjusted under 35 U.S.C. 154(b) by 72 days.

(21) Appl. No.: 13/644,889

(22) Filed: Oct. 4, 2012

(65) Prior Publication Data

US 2013/0202674 A1 Aug. 8, 2013

Related U.S. Application Data

(60) Provisional application No. 61/594,898, filed on Feb. 3, 2012.

(51) Int. Cl.
| | | |
|---|---|---|
| *A61K 9/70* | (2006.01) | |
| *A61K 9/00* | (2006.01) | |
| *A61L 24/00* | (2006.01) | |
| *A61L 24/10* | (2006.01) | |
| *A61L 15/32* | (2006.01) | |
| *A61L 15/34* | (2006.01) | |
| *A61L 15/58* | (2006.01) | |
| *A61L 15/64* | (2006.01) | |

(52) U.S. Cl.
CPC .............. *A61K 9/7023* (2013.01); *A61K 9/0014* (2013.01); *A61L 24/0042* (2013.01); *A61L 24/106* (2013.01); *A61L 24/001* (2013.01); *A61L 2300/418* (2013.01); *A61L 2400/04* (2013.01); *A61L 2400/06* (2013.01); *A61L 15/32* (2013.01); *A61L 15/34* (2013.01); *A61L 15/58* (2013.01); *A61L 15/64* (2013.01)

(58) Field of Classification Search
None
See application file for complete search history.

(56) References Cited

U.S. PATENT DOCUMENTS

| | | |
|---|---|---|
| 2,492,458 A | 12/1949 | Bering, Jr. |
| 2,533,004 A | 12/1950 | Ferry et al. |
| 2,576,006 A * | 11/1951 | Ferry et al. ............... 156/160 |
| 3,523,807 A | 8/1970 | Gerendas |
| 4,347,841 A | 9/1982 | Benyó et al. |
| 4,790,819 A | 12/1988 | Li et al. |
| 4,909,251 A | 3/1990 | Seelich |
| 5,209,776 A | 5/1993 | Bass et al. |
| 5,219,328 A | 6/1993 | Morse et al. |
| 5,290,552 A | 3/1994 | Sierra et al. |
| 5,292,362 A | 3/1994 | Bass et al. |
| 5,318,524 A | 6/1994 | Morse et al. |
| 5,407,671 A | 4/1995 | Heimburger et al. |
| 5,437,292 A | 8/1995 | Kipshidze et al. |
| 5,464,471 A | 11/1995 | Whalen et al. |
| 5,549,904 A | 8/1996 | Juergensen et al. |
| 5,585,007 A | 12/1996 | Antanavich et al. |
| 5,630,842 A | 5/1997 | Brodniewicz |
| 5,631,011 A | 5/1997 | Wadström |
| 5,643,192 A | 7/1997 | Hirsh et al. |
| 5,649,959 A | 7/1997 | Hannam et al. |
| 5,702,715 A | 12/1997 | Nikolaychik et al. |
| 5,716,645 A | 2/1998 | Tse et al. |
| 5,736,132 A | 4/1998 | Juergensen et al. |
| 5,739,288 A | 4/1998 | Edwardson et al. |
| 5,750,657 A | 5/1998 | Edwardson et al. |
| 5,763,410 A | 6/1998 | Edwardson et al. |
| 5,763,411 A | 6/1998 | Edwardson et al. |
| 5,770,194 A | 6/1998 | Edwardson et al. |
| 5,773,418 A | 6/1998 | Edwardson et al. |
| 5,788,662 A | 8/1998 | Antanavich et al. |
| 5,795,571 A | 8/1998 | Cederholm-Williams et al. |
| 5,795,780 A | 8/1998 | Cederholm-Williams et al. |
| 5,804,428 A | 9/1998 | Edwardson et al. |
| 5,844,087 A | 12/1998 | Zimmerman et al. |
| 5,883,078 A | 3/1999 | Seelich et al. |
| 5,962,026 A | 10/1999 | Edwardson et al. |
| 5,962,420 A | 10/1999 | Edwardson et al. |
| 5,977,313 A | 11/1999 | Heath et al. |
| 5,985,315 A | 11/1999 | Patat et al. |
| 6,007,811 A | 12/1999 | Sawyer et al. |
| 6,015,474 A | 1/2000 | Stedronsky |
| 6,019,993 A | 2/2000 | Bal |
| 6,043,407 A | 3/2000 | Lodhi et al. |
| 6,048,966 A | 4/2000 | Edwardson et al. |
| 6,063,297 A | 5/2000 | Antanavich et al. |
| 6,074,663 A | 6/2000 | Delmotte et al. |
| 6,077,507 A | 6/2000 | Edwardson et al. |

(Continued)

FOREIGN PATENT DOCUMENTS

| | | |
|---|---|---|
| WO | WO 03/092756 A1 | 11/2003 |
| WO | WO 2006042311 A2 * | 4/2006 |
| WO | WO 2012/030570 A1 | 3/2012 |

OTHER PUBLICATIONS

Radosevich et al., "Fibrin sealant: scientific rationale, production methods, properties, and current clinical use," *Vox Sanguinis* (1997) 72(3):133-143.

(Continued)

*Primary Examiner* — David J Blanchard
*Assistant Examiner* — Daniel F Coughlin
(74) *Attorney, Agent, or Firm* — Wolf, Greenfield & Sacks, P.C.

(57) ABSTRACT

Tissue patches and associated systems and methods are described. Certain embodiments are related to inventive systems and methods in which tissue patches can be made quickly and robustly without the use of complicated fabrication or sterilization equipment.

41 Claims, 11 Drawing Sheets

(56) References Cited

U.S. PATENT DOCUMENTS

| | | | |
|---|---|---|---|
| 6,162,241 A | 12/2000 | Coury et al. | |
| 6,200,587 B1 | 3/2001 | Soe et al. | |
| 6,214,338 B1 | 4/2001 | Antanavich et al. | |
| 6,251,370 B1 | 6/2001 | Uchida et al. | |
| 6,258,872 B1 | 7/2001 | Stedronsky | |
| 6,262,236 B1 | 7/2001 | Edwardson et al. | |
| 6,268,483 B1 | 7/2001 | Edwardson et al. | |
| 6,342,250 B1 | 1/2002 | Masters | |
| 6,368,298 B1 | 4/2002 | Beretta et al. | |
| 6,395,288 B1 | 5/2002 | Woolverton | |
| 6,440,427 B1 | 8/2002 | Wadström | |
| 6,444,228 B1 | 9/2002 | Baugh et al. | |
| 6,447,774 B1 | 9/2002 | Metzner | |
| 6,492,494 B1 | 12/2002 | Cederholm-Williams | |
| 6,500,427 B1 | 12/2002 | Heimburger et al. | |
| 6,503,527 B1 | 1/2003 | Whitmore | |
| 6,506,365 B1 | 1/2003 | Redl et al. | |
| 6,528,483 B2 | 3/2003 | Beaulieu et al. | |
| 6,534,693 B2 | 3/2003 | Fischell et al. | |
| 6,548,729 B1 | 4/2003 | Seelich et al. | |
| 6,559,119 B1 | 5/2003 | Burgess | |
| 6,576,685 B2 | 6/2003 | Stedronsky | |
| 6,579,537 B2 | 6/2003 | Seelich et al. | |
| 6,613,324 B1 | 9/2003 | Blombäck et al. | |
| 6,613,325 B1 | 9/2003 | Amery et al. | |
| 6,699,484 B2 | 3/2004 | Whitmore et al. | |
| 6,706,780 B2 | 3/2004 | Goldberg et al. | |
| 6,733,774 B2 | 5/2004 | Stimmeder | |
| 6,762,336 B1 | 7/2004 | MacPhee et al. | |
| 6,780,411 B2 | 8/2004 | Lewis, Jr. et al. | |
| 6,875,796 B2 | 4/2005 | Stedronsky | |
| 6,891,077 B2 | 5/2005 | Rothwell et al. | |
| 6,916,911 B1 | 7/2005 | Bar et al. | |
| 6,921,532 B1 | 7/2005 | Austin et al. | |
| 6,942,880 B1 | 9/2005 | Dolecek | |
| 6,979,307 B2 | 12/2005 | Beretta et al. | |
| 7,045,601 B2 | 5/2006 | Metzner et al. | |
| 7,052,713 B2 | 5/2006 | Stimmeder | |
| RE39,192 E | 7/2006 | MacPhee et al. | |
| 7,091,015 B1 | 8/2006 | Redl et al. | |
| 7,091,325 B2 | 8/2006 | Redl et al. | |
| RE39,298 E | 9/2006 | MacPhee et al. | |
| RE39,321 E | 10/2006 | MacPhee et al. | |
| 7,141,428 B2 | 11/2006 | McKerracher | |
| 7,189,410 B1 | 3/2007 | Drohan et al. | |
| 7,196,054 B1 | 3/2007 | Drohan et al. | |
| 7,198,786 B2 | 4/2007 | Redl et al. | |
| 7,208,179 B1 | 4/2007 | Drohan et al. | |
| 7,211,651 B2 | 5/2007 | Pathak | |
| 7,226,657 B1 | 6/2007 | Delmotte et al. | |
| 7,229,633 B2 | 6/2007 | Austin et al. | |
| 7,229,959 B1 | 6/2007 | Drohan et al. | |
| 7,235,255 B2 | 6/2007 | Austin et al. | |
| 7,241,603 B2 | 7/2007 | Seelich et al. | |
| 7,276,235 B2 | 10/2007 | Metzner et al. | |
| 7,285,580 B2 | 10/2007 | Stedronsky | |
| 7,326,412 B2 | 2/2008 | Redl | |
| 7,399,483 B2 | 7/2008 | Stimmeder | |
| 7,427,607 B2 | 9/2008 | Suzuki | |
| 7,459,295 B2 | 12/2008 | Redl et al. | |
| 7,494,971 B2 | 2/2009 | Eibl | |
| 7,605,232 B2 | 10/2009 | Pathak | |
| 7,662,409 B2 | 2/2010 | Masters | |
| 7,745,106 B2 | 6/2010 | Beretta et al. | |
| 7,811,607 B2 | 10/2010 | Baugh et al. | |
| 7,838,039 B2 | 11/2010 | Baugh et al. | |
| 7,867,519 B2 | 1/2011 | de Maat et al. | |
| 7,892,802 B2 | 2/2011 | Redl et al. | |
| 7,934,603 B2 | 5/2011 | Eaton et al. | |
| 7,968,682 B2 | 6/2011 | Farrell | |
| 8,299,316 B2 | 10/2012 | Van Holten et al. | |
| 2006/0204555 A1 | 9/2006 | Yang et al. | |
| 2006/0235121 A1 | 10/2006 | Burch | |
| 2007/0160543 A1 | 7/2007 | Moller | |
| 2008/0091235 A1* | 4/2008 | Sirota | 606/215 |
| 2009/0075891 A1 | 3/2009 | MacPhee et al. | |
| 2009/0239300 A1* | 9/2009 | Awaji et al. | 435/377 |
| 2010/0316712 A1* | 12/2010 | Nangia et al. | 424/472 |
| 2011/0066182 A1 | 3/2011 | Falus | |
| 2011/0071499 A1* | 3/2011 | Hakimimehr et al. | 604/509 |
| 2011/0196421 A1 | 8/2011 | MacPhee et al. | |
| 2012/0070485 A1* | 3/2012 | Soldani et al. | 424/443 |
| 2013/0202656 A1 | 8/2013 | Ericson | |
| 2013/0202675 A1 | 8/2013 | Ericson | |

OTHER PUBLICATIONS

Invitation to Pay Additional Fees for PCT/US2013/024322 mailed May 29, 2013.

International Search Report and Written Opinion for PCT/US2013/024322 mailed Aug. 12, 2013.

Browdie et al., "Tests of experimental tissue adhesive sealants," *Texas Heart Institute Journal* (2007) 34: 313-317.

Dempfle et al., "Impact of fibrinogen concentration in severely ill patients on mechanical properties of whole blood clots," *Blood Coagul Fibrinolysis* (2008) 19: 765-770.

Elvin et al., "Photochemical fabrication of a highly elastic and adhesive surgical tissue sealant," *European Cells and Materials* (2010) vol. 20 Suppl. 3: 71 ISSN 1473-2262.

Pal et al., "Rosin an important polymer for drug delivery: A short review," International Journal of Pharmaceutical Sciences Review and Research (Jul.-Aug. 2010) vol. 3: 35-37, Issue 1, ISSN 0976-044X.

Satturwar et al. "Biodegradation and in vivo biocompatibility of rosin: a natural film-forming polymer" APPS PharmSciTech (2003) 4 (4): 1-6, Article 55 (http://www.aapspharmscitech.org).

Office Communication mailed Feb. 25, 2014 for U.S. Appl. No. 13/644,907.

Cheng, et al., A review of three stand-alone topical thrombins for surgical hemostasis. Clin Ther. Jan. 2009;31(1):32-41. doi: 10.1016/j.clinthera.2009.01.005.

Sierra et al., Failure characteristics of multiple-component fibrin-based adhesives. J Biomed Mater Res. Jan. 2002;59(1):1-11.

* cited by examiner

TISSUE PATCH

RELATED APPLICATIONS

This application claims priority under 35 U.S.C. §119(e) to U.S. Provisional Patent Application Ser. No. 61/594,898, filed Feb. 3, 2012, and entitled "Tissue Patches and Associated Systems and Methods," which is incorporated herein by reference in its entirety for all purposes.

TECHNICAL FIELD

Tissue patches and associated systems and methods are generally described.

BACKGROUND

Hemostatic agents and tissue sealants are routinely used to prevent excess blood loss and to reconstruct tissue during surgical repair. Fibrin glue was approved by the FDA in the 1990's and can be used to impart topical hemostasis, provide sealant properties that are suitable is some clinical applications, and promote tissue approximation. Fibrin glue mimics the final steps of the coagulation cascade. In the presence of thrombin, fibrinogen is converted to fibrin. Thrombin also activates Factor XIII, which stabilizes the clot, by promoting polymerization and/or cross-linking of the fibrin chains to form long fibrin strands. This process usually occurs in the presence of calcium ions. It proceeds independently from the remainder of the coagulation cascade, and provides some degree of hemostasis even with defects in other portions of this pathway. There is subsequent proliferation of fibroblasts and formation of granulation tissue within hours of clot polymerization. The fibrin clot caused by the sealant degrades physiologically. Fibrin sealant can be manufactured from pooled or single source donors.

The composition of fibrin glue products varies, but they generally include a 2-vial system containing fibrinogen, thrombin, factor XIII, and calcium (typically calcium chloride). Fibrin glue products generally include a first component including fibrinogen and Factor XIII (analogous to the "resin" portion of a two part epoxy kit) and a second component including thrombin in a $CaCl_2$ solution (analogous to the "catalyst" component of an epoxy kit). The components may be applied sequentially or simultaneously to the repair site, for example, using a double-barrel syringe onto a dry tissue bed. Prior to polymerization, the fibrin sealants acts as a flowable, sprayable "sticky" liquid that is designed to adhere to wet surfaces. Once polymerized in situ by the addition of thrombin and calcium it becomes a semi-rigid, hemostatic mass intended to hold tissue or materials in a desired configuration. Preparation takes approximately 15 minutes and once the components have been mixed, the product is available for use for 4 hours before the thrombin degrades. Used within their limitations, tissue sealants offer clinicians a valuable and versatile tool for the treatment of bleeding.

However, currently available tissue sealants generally do not perform well in wet or "bleeding" applications. Current commercially available tissue sealants and hemostatic agents are generally either too slow, too cumbersome, lack optimum adhesive properties, or lack the tensile strength required for suturing and preventing arterial blood loss. In addition, many currently available sealants do not have the mechanical strength to address many clinical wound closure demands. Accordingly, a tissue patch that addresses each of these shortcomings would be desirable.

SUMMARY

Tissue patches and associated systems and methods are provided. The subject matter of the present invention involves, in some cases, interrelated products, alternative solutions to a particular problem, and/or a plurality of different uses of one or more systems and/or articles.

In one aspect, a patch is provided. The patch comprises, in certain embodiments, a primer region comprising a resin; and a solid matrix comprising fibrin and/or fibrinogen positioned over at least a portion of the primer region, wherein the patch is sterile and configured for application to a tissue surface.

The patch comprises, in some embodiments, a primer region comprising a metal oxide, a metalloid oxide, and/or a zinc-containing composition; and a solid matrix comprising fibrin positioned over at least a portion of the primer region, wherein the patch is configured for application to a tissue surface.

In certain embodiments, the patch comprises an unsupported solid matrix formed of fibrin and/or fibrinogen, wherein the unsupported solid matrix has a Young's modulus of about 10 GPa or less after sterilization using gamma radiation at an intensity of 30 kGy, and wherein the patch is sterile and configured for application to a tissue surface.

The patch comprises, in some embodiments, an unsupported solid matrix formed of fibrin and/or fibrinogen, wherein the fibrin within the unsupported solid matrix is cross-linked to a degree such that, after submerging the unsupported solid matrix in an 8M aqueous solution of urea at 25° C., the unsupported solid matrix retains its structural integrity over a period of at least about 2 hours, and the patch is sterile and configured for application to a tissue surface.

In some embodiments, the patch comprises an unsupported solid matrix formed of fibrin and/or fibrinogen, wherein the fibrin within the unsupported solid matrix is cross-linked to a degree such that, after submerging the unsupported solid matrix in a 6M aqueous solution of urea at 25° C., the unsupported solid matrix retains its structural integrity over a period of at least about 2 hours, and the patch is sterile and configured for application to a tissue surface.

In certain embodiments, the patch comprises a primer region comprising rosin; and a solid matrix positioned over at least a portion of the primer region, wherein the patch is configured for application to a tissue surface.

The patch comprises, in certain embodiments, a primer region comprising at least one of a water-activated polymeric adhesive, a cellulose derivative, an oil, and a metal-containing species; and a solid matrix positioned over at least a portion of the primer region, wherein the patch is configured for application to a tissue surface.

In another aspect, a kit is provided. In certain embodiments, the kit comprises a syringe configured to receive a quantity of blood or blood component from a subject, a filter configured to separate at least a portion of fibrin and/or fibrinogen within the quantity of blood or blood component from at least a portion of a liquid component of the quantity of blood or blood component, and a curing agent capable of activating the polymerization of fibrinogen to fibrin.

In some embodiments, the kit comprises a filter comprising a plurality pores, a liquid-containing composition comprising fibrin and/or fibrinogen, and a curing agent comprising thrombin.

The kit comprises, in certain embodiments, a solid matrix comprising fibrin and/or fibrinogen, wherein the solid matrix is sterile and configured for application to a tissue surface; and a primer composition comprising at least one of a water-activated polymeric adhesive, a cellulose derivative, an oil, and a metal-containing species.

In another aspect, a system for producing a tissue patch is provided. The system comprises, in certain embodiments, a syringe configured for containing a quantity of blood or blood component from a subject, and containing a curing agent capable of activating the polymerization of fibrinogen to fibrin. The system also comprises, in certain embodiments, a filter configured to separate at least a portion of fibrin and/or fibrinogen within the quantity of blood or blood component from at least a portion of a liquid component of the quantity of blood or blood component, wherein the filter is contained within the syringe and/or attached to a discharge port of the syringe.

In another aspect, a method of preparing a tissue adherent patch is provided. In certain embodiments, the method comprises applying a compressive force to a liquid containing composition comprising fibrin and/or fibrinogen; passing at least a portion of a liquid component of the composition through a filter so that at least a portion of the fibrin and/or fibrinogen is separated from the at least a portion of the liquid component; and polymerizing the fibrinogen to form fibrin and/or cross-linking the fibrin to form a solid matrix comprising cross-linked fibrin, wherein the tissue adherent patch comprises or is formed from the solid matrix.

In one set of embodiments, the method comprises applying a compressive force to a liquid containing composition comprising fibrin and/or fibrinogen within a chamber; and polymerizing the fibrinogen to form fibrin and/or cross-linking the fibrin to form a solid matrix comprising cross-linked fibrin, wherein the tissue adherent patch comprises or is formed from the solid matrix.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Tissue patches and associated systems and methods are provided. Certain embodiments are related to inventive systems and methods in which tissue patches can be made quickly and robustly without the use of complicated fabrication or sterilization equipment. For example, in some embodiments, tissue patches are made by applying a compressive force to a liquid-containing composition comprising fibrinogen (and/or fibrin) between two surfaces (e.g., within a syringe or other chamber). A filter can be placed within or near the volume in which the compressive force is applied to the liquid-containing composition such that unwanted material (e.g., some liquid components (e.g., water), blood cells, etc.) is passed through the filter while desirable components (e.g., fibrin and/or fibrinogen) are retained by the filter to form the patch. In this way, the concentration of fibrin (and/or fibrinogen) can be increased, potentially substantially, as the compressive force is applied to the liquid-containing composition. In addition, in some embodiments, at least a portion of the fibrinogen and/or fibrin can chemically react (e.g., the fibrinogen can polymerize to form fibrin and/or the fibrin can cross-link) before, during, and/or after application of the compressive force. Reaction and concentration via application of the compressive force (e.g., by removing at least a portion of the non-fibrin and/or non-fibrinogen components, such as liquid components (e.g., water), blood cells, and the like) can lead to the formation of a highly-concentrated, mechanically robust patch that can be handled relatively easily and provide good structural reinforcement at a wet site, such as a bleeding wound. In certain embodiments, additional advantage, economy, convenience, and/or safety is gained by the use of autologous whole blood as the liquid-containing composition to which a compressive force is applied to form the patch.

In addition, inventive systems and methods for applying patches to tissue are described. For example, in certain embodiments, the tissue patches described herein include a primer region (e.g., a primer region is formed on a patch during use and prior to application) that achieves effective immobilization of the patch (in some instances, without the need to apply much or any external pressure) while allowing the patch to integrate with the underlying tissue. In certain embodiments, the primer region comprises a naturally derived resin such as pine rosin, a zinc-containing material such as zinc oxide, and/or a metal oxide and/or metalloid oxide. In certain embodiments, thrombin (e.g., a thrombin solution, thrombin powder, or thrombin in any other suitable form) can be applied over the primer region to further enhance the ability of the patch to adhere to tissue.

Figure 1A:
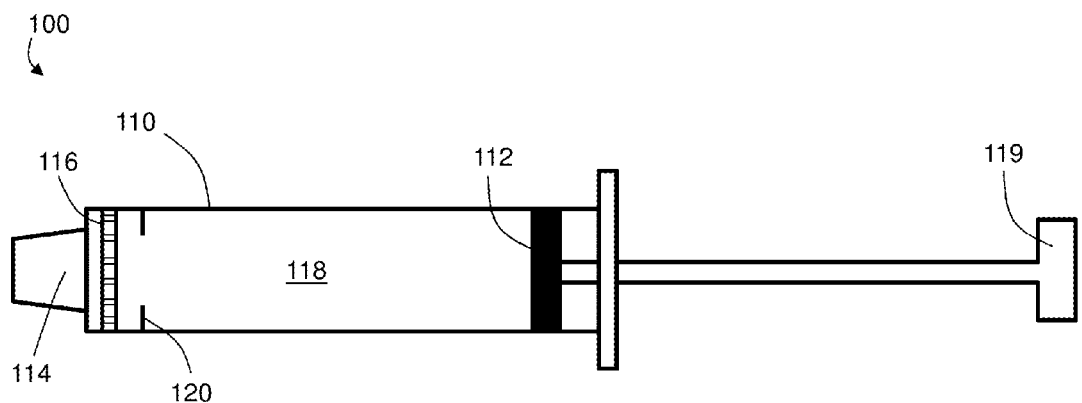
FIGS. 1A-1C are cross-sectional schematic illustrations of a system for producing a tissue patch, according to one set of embodiments.
Figure 1B:
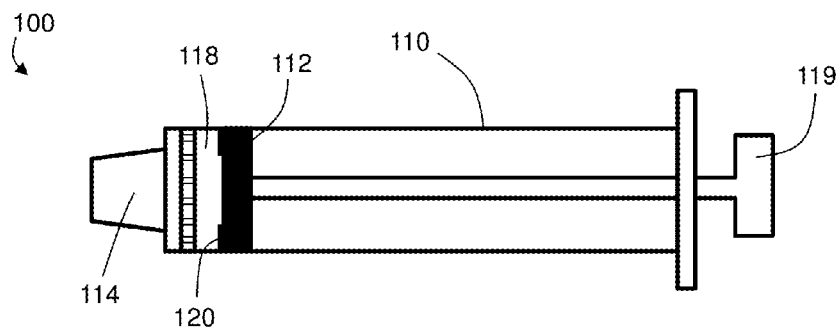

FIGS. 1A-1B are exemplary schematic illustrations outlining a system and method for the formation of a tissue patch, according to one set of embodiments. In FIGS. 1A-1B, syringe 100 comprises chamber 110. A liquid-containing composition comprising fibrin and/or fibrinogen (e.g., blood or a non-blood fibrin and/or fibrinogen suspension) can be transported into and/or provided within chamber 110. The fibrin and/or fibrinogen within the liquid-containing composition can be capable of reacting (e.g., polymerizing and/or cross-linking) within chamber 110 to form a mechanically-stable tissue patch material. Chemical reaction of the fibrin and/or fibrinogen can be initiated, in certain embodiments, for example, by including a curing agent such as thrombin and/or a calcium-containing compound (e.g., $CaCl_2$) within chamber 110.

In certain embodiments, the filter can be provided at or near a discharge end of the chamber. For example, in FIG. 1A, filter 116 is provided at or near outlet 114 of chamber 110 (within or outside chamber 110). Filter 116 can be configured to inhibit or essentially prevent the through-flow of components that are useful in forming the tissue patch (e.g., fibrin and/or fibrinogen, and/or other useful materials), thereby retaining the useful components at or near the filter and within the chamber. In addition, filter 116 can be configured to allow at least a portion of the components of the liquid-containing composition that are not useful for forming the tissue patch (e.g., liquid components (e.g., water), blood cells, or other similar components) to be passed through the filter and out of the chamber during the application of the compressive force (described below). Chamber 110 and filter 116 can assume a variety of geometries and can be made of a variety of materials, as described in more detail below.

In some embodiments, the tissue patch can be formed by applying a compressive force to the liquid-containing composition within chamber 110, for example, by actuating moveable wall 112 toward outlet 114. In FIG. 1A, for example, the volume 118 occupied by the liquid-containing composition is relatively large because wall 112 has not yet been actuated toward outlet 114. In FIG. 1B, on the other hand, a compressive force has been applied to chamber 110 by moving wall 112 toward outlet 114, thereby passing at least a portion of the liquid-containing composition (e.g., liquid components (e.g., water), blood cells, etc.) through filter 116 and out of chamber 110, and reducing the volume 118 of liquid-containing composition within chamber 110 and concentrating the fibrin, fibrinogen, and/or other patch-forming components within the liquid-containing composition.

Wall 112 can be actuated using any suitable mechanism. For example, in certain embodiments, wall 112 can be actuated by manually applying a force to stopper 119. In other embodiments, wall 112 can be actuated using a trigger mechanism.

To illustrate one mode of operation, in one particular set of embodiments, a liquid-containing composition comprising fibrin and/or fibrinogen (and/or other components) as well as other components such as water, is provided to chamber 110. For example, a fibrin solution or blood can be provided to chamber 110. Chamber 110 can include an initiator, such as thrombin, which can initiate the polymerization of fibrinogen to fibrin and/or the cross-linking of fibrin. In certain embodiments, the polymerization and/or cross-linking of the fibrinogen and/or fibrin can produce fibrin molecules that are sufficiently large to be retained by filter 116. Wall 112 can be actuated toward outlet 114 such that at least a portion of the liquid (e.g., water) and/or other undesirable components (e.g., blood cells, if present, and/or other non-fibrin and/or non-fibrinogen components) are transported through filter 116 and out of outlet 114 while at least a portion of the fibrin and/or fibrinogen are retained by the filter to form a relatively concentrated matrix of material between wall 112 and filter 116. The matrix material can be solidified to form a tissue patch, as described further below, in certain embodiments.

The chamber can comprise, in certain embodiments, a stop configured to prevent the moveable wall from reducing the volume of the chamber below a threshold value. For example, in FIGS. 1A-1B, chamber 110 includes stop 120. Stop 120 can be configured to restrict wall 112 from reducing the volume of the liquid-containing composition below the amount illustrated in FIG. 1B. Stop 120 can also be configured to restrict wall 112 from making contact with filter 116. By configuring chamber 110 and stop 120 in this way, one can reduce or eliminate the risk of applying the compressive force to the liquid-containing composition to an excessive or insufficient degree, which can help one control the final thickness of the patch.

Figure 1C:
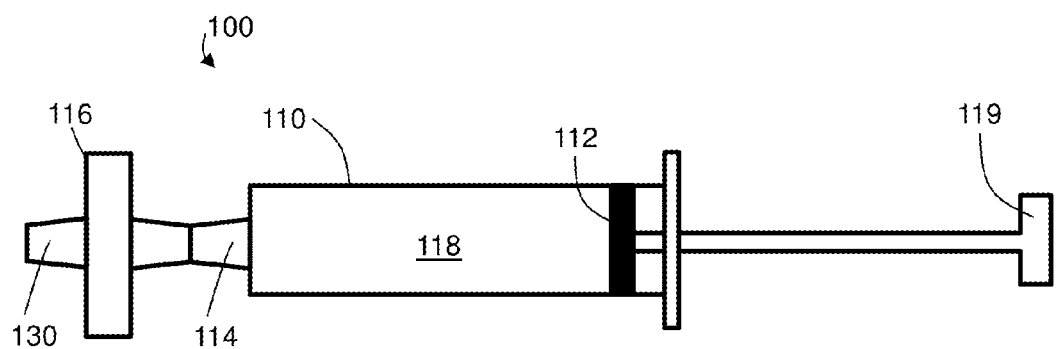

In certain embodiments, rather than locating filter 116 within chamber 110, filter 116 can be positioned outside the chamber. For example, FIG. 1C is a cross-sectional schematic illustration of one set of embodiments in which filter 116 is fluidically connected to outlet 114 of syringe 100. In one particular set of embodiments, syringe 100 can comprise a standard syringe with a Leur-lok outlet port, and filter 116 can comprise a standard syringe disc filter cartridge. Filter 116 can also include, in some embodiments, an outlet port 130, which can be configured to allow through-flow components (e.g., water, blood cells, etc.) to be transported out of the system.

In certain embodiments, at least a portion of the fibrin and/or fibrinogen within the liquid-containing composition can chemically react (e.g., polymerize and/or cross-link) within chamber 110. Chemical reaction of the fibrin and/or fibrinogen can occur before, during, and/or after application of the compressive force. In certain embodiments, at least a portion of the fibrinogen within chamber 110 can be polymerized to form fibrin, before, during, and/or after application of the compressive force. In some embodiments, at least a portion of the fibrin within chamber 110 can be further polymerized and/or cross-linked, before, during, and/or after application of the compressive force. Chemical reaction of the fibrin and/or fibrinogen can be initiated, in certain embodiments, via a curing agent such as thrombin and/or a calcium-containing compound (e.g., $CaCl_2$), as discussed in more detail below.

In some embodiments (e.g., in embodiments in which a large amount of curing agent such as thrombin is present), at least a portion of the chemical reaction of the fibrin and and/or fibrinogen can occur during at least a portion of the time during which the compressive force is applied. Simultaneous application of the compressive force and reaction of the fibrin and/or fibrinogen can ensure, in certain embodiments, that the liquid-containing composition retains a suitable viscosity during the application of the compressive force. For example, if the fibrin and/or fibrinogen were polymerized and/or cross-linked to a large degree (e.g., completely) prior to applying the compressive force, application of the compressive force would be difficult due to the high resistance to flow of the viscous polymerized/gelled liquid-containing composition. Simultaneous application of the compressive force and reaction can also ensure that fibrinogen and/or fibrin are not transported out of the chamber to a large degree (e.g., by polymerizing and/or cross-linking the fibrinogen and/or fibrin to form relatively large molecules before relatively short molecules have a chance to be transported out of the chamber). By inhibiting the transport of fibrinogen and/or fibrin out of the chamber, relatively large concentrations of fibrin and/or fibrinogen within the final patch can be achieved.

While chamber 110 in FIGS. 1A-1C is part of a syringe, it should be understood that the invention is not so limited. The use of a syringe can be advantageous, in certain cases, because syringes are readily available, inexpensive, and relatively easy to sterilize. Of course, in other embodiments, other types of chambers may be used to form the tissue patches described herein. In certain embodiments, the chamber is configured such that its volume may be reduced, for example, by moving a wall of the chamber. In certain embodiments, the chamber is at least partially enclosed, including a movable wall and an outlet through which material that is not useful for forming the tissue patch is transported. In some embodiments, the chamber can be configured to include a stop, as illustrated in the syringe chamber in FIGS. 1A-1B, to control the thickness of the patch that is produced. The moveable wall of the chamber (or any other wall of the chamber, or the filter) can be shaped, in some cases to produce a tissue patch with a desirable surface geometry. In certain embodiments, the chamber comprises a deformable bag, and a filter could be positioned at or near an outlet through which the liquid-containing composition is transported. One of ordinary skill in the art, given the present disclosure, could envision a variety of other suitable chamber configurations that could be used to produce the tissue patches described herein.

Chambers suitable for use in the invention can be of any desired size and can have any suitable geometry. In certain embodiments, the chamber can be configured to contain, prior to application of the compression step, at least about 1 milliliter, at least about 10 milliliters, at least about 100 milliliters, at least about 1 liter, or more (and/or, in certain embodiments, less than 10 liters or less than 1 liter). The cross-sectional shape of the chamber can be substantially circular, elliptical, polygonal (e.g., including any number of sides such as in the form of a triangle, a quadrilateral (e.g., rectangular or substantially square), etc.), irregularly-shaped, or any other suitable shape.

In addition, filter 116 can assume a variety of configurations. For example, in certain embodiments, the filter comprises a membrane disc. The membrane disc can comprise, for example, a plurality of pores. The plurality of pores can be configured and sized to separate fibrin and/or fibrinogen from at least one non-fibrin and non-fibrinogen component (e.g., liquid (e.g., water), blood cells, and the like). In one set of embodiments (including some embodiments in which the liquid-containing composition from which the tissue patch is formed comprises blood, such as the blood sample of a subject), the filter can be configured to separate a plasma component (e.g., a plasma component within blood, which might comprise fibrin and/or fibrinogen) from at least one non-plasma component (e.g., blood cells and/or other components).

The pores within filter 116 can, in certain embodiments, comprise substantially straight passageways through a bulk filter material (as opposed to tortuous pathways that might be observed, for example, in a porous sponge). That is to say, one or more of the pores within the filter can be configured to pass from one side of the filter to the other, with a substantially constant cross-sectional geometry along substantially the entire length of the hole. For example, in one set of embodiments, filter 116 comprises a track-etched membrane. The pores within the filter can have any suitable cross-sectional shape (e.g., substantially circular, substantially elliptical, substantially square, triangular, irregular).

The pores within the filter can also be of any suitable size that is capable of achieving the desired separation (i.e. a desired level of liquid removal and retention of tissue patch forming solids). In certain embodiments, at least about 50%, at least about 75%, or at least about 90% of the pores in the filter have maximum cross-sectional dimensions, of between about 100 micrometers and about 10 millimeters, or between about 100 micrometers and about 5 millimeters, or between about 250 micrometers and 1.5 millimeters. In some embodiments, the average pore size of the pores within the filter is between about 100 micrometers and about 10 millimeters, between about 100 micrometers and about 5 millimeters, or between about 250 micrometers and 1.5 millimeters.

In certain embodiments, at least about 50%, at least about 75%, at least about 90%, at least about 95%, or at least about 99% of the total volume of the pores in the filter is made up of pores with maximum cross-sectional dimensions, of between about 100 micrometers and about 10 millimeters, or between about 100 micrometers and about 5 millimeters, or between about 250 micrometers and 1.5 millimeters. As used herein, the volume of a pore corresponds to the volume of the voice space that is defined by the pore. For example, in a filter with cylindrical pores, the volume of any given pore is determined by calculating the volume of the cylinder defined by the pore. Volumes of individual pores can be determined by submerging the filter in a liquid and measuring the volume of liquid that is displaced, before and after individual pores are filled with a material that plugs the pores. The total volume of the pores can be calculated by plugging all of the pores, submerging the plugged filter in a fluid and measuring the volume of fluid that is displaced, and comparing this measured volume to the volume of fluid that is displaced when the filter is submerged in the fluid with all of the pores unplugged. The formula for calculating the percentage of pore volume made up of pores with maximum cross-sectional dimensions of between about X and about Y, one would sum the volumes of all of the pores with maximum cross-sectional dimensions between about X and about Y, divide this sum by the total volume of the pores in the filter, and multiply by 100%.

The pores can be arranged to have any suitable density. In certain embodiments, the density of the pores within the filter can be, for example, between about 10 and 1000, between 50 and 500, or between 100 and 200 pores per square inch.

All or part of filter 116 can be formed from a variety of suitable materials. For example, in certain embodiments, filter 116 comprises a metal such as aluminum, steel (e.g., stainless steel such as surgical stainless steel), titanium, and the like. In certain embodiments, filter 116 comprises one or more polymers. Filter 116 can comprise, in some embodiment, one or more ceramics (carbide ceramics, boride ceramics, etc.). Filter 116 might also comprise a mixture (e.g., alloy or composite) or two or more of these materials. In certain embodiments, the material from which the filter is fabricated can be selected to maintain its mechanical integrity during the application of the compressive force used to produce the patch.

Figure 3A:
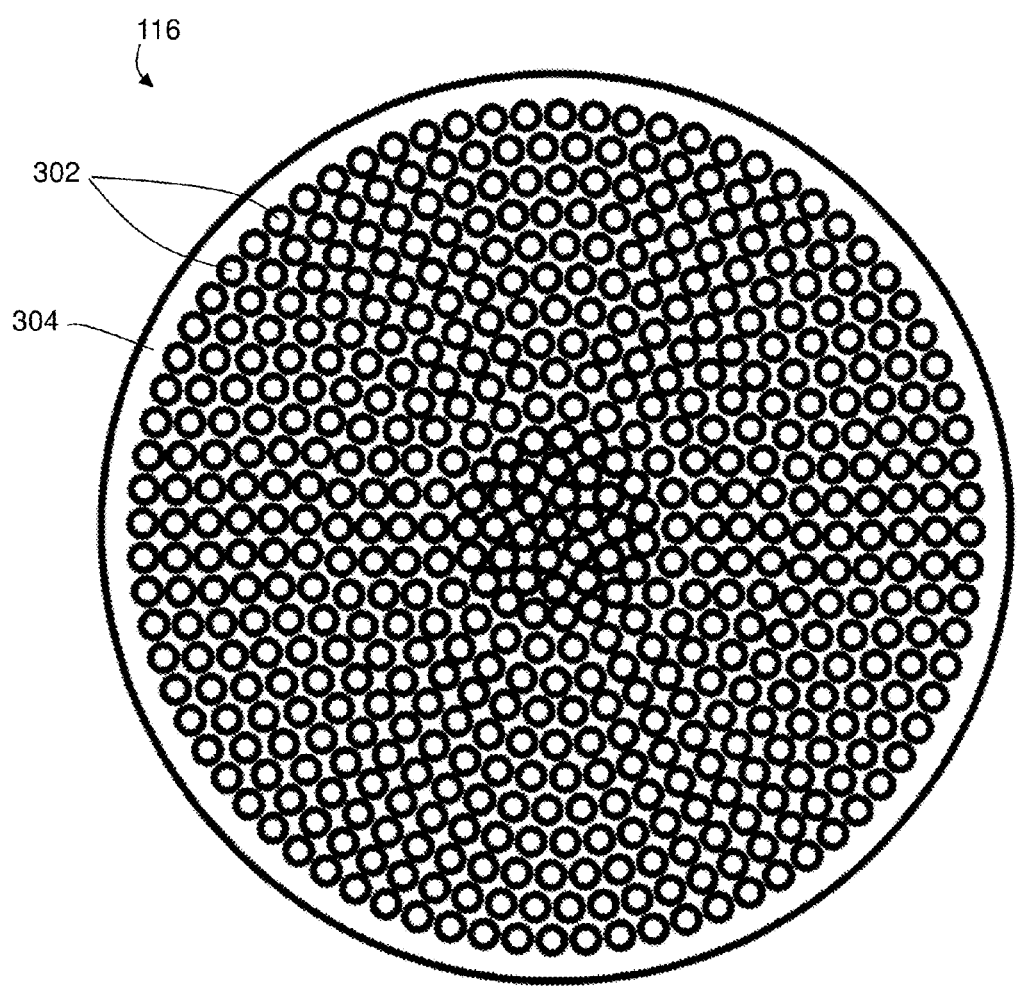
FIG. 3A is a schematic illustration of an exemplary filter disc, used in association with one set of embodiments.

FIG. 3A is an exemplary schematic illustration of an exemplary disc filter that can be used in association with the invention, in certain embodiments. In FIG. 3A, filter 116 includes a plurality of pores 302 formed in a bulk material 304.

A variety of liquid media are potentially suitable for forming the tissue patches described herein. In certain embodiments, the liquid-containing composition used to form the patch comprises fibrin and/or fibrinogen, which can be subjected to a compressive force and/or reacted to form the tissue patch. For example, the liquid-containing composition can comprise, in certain cases, whole blood and/or a plasma component of whole blood. In certain embodiments, the liquid-containing composition can comprise a blood component, such as fibrin and/or fibrinogen or a fibrin- and/or fibrinogen-containing fraction of blood. In some embodiments, the liquid-containing composition can comprise a suspension (e.g., aqueous or non-aqueous) of fibrin and/or fibrinogen. As one particular example, in certain embodiments, the liquid-containing composition can comprise a suspension of fibrinogen formed by adding lyophilized fibrinogen to a liquid (e.g., water, saline, or any other suitable liquid) to form a fibrinogen suspension.

In certain embodiments, the liquid-containing composition supplied to the chamber (e.g., a chamber within a syringe, or any other suitable chamber) includes autologous blood. For example, in certain embodiments, the liquid-containing composition comprises at least a part of a blood sample removed from a subject. The blood sample can be transported to the chamber (e.g., directly or after separating one or more components of the blood from the remaining portion of the blood) where it can be subject to a compressive force. The fibrin and/or fibrinogen within the sample can be reacted to form a tissue patch. In certain embodiments, the tissue patch can be applied to the same subject from which the blood sample was removed.

Optionally, the liquid-containing composition can include (e.g., naturally or via supplementation) other components such as coagulation factors, preservatives, and/or supplemental drugs (e.g., antibiotics, anesthetics, and the like). For example, when a sample of whole blood is used as the liquid-containing composition, the sample might inherently contain coagulation factors naturally present in the blood sample. In some embodiments, a preservative might be added to the blood sample prior to its use as the liquid-containing composition. In certain embodiments in which blood is used as a the liquid-containing composition, the blood can be transported essentially directly from the subject to the chamber, without chemical supplementation. In some embodiments, the liquid containing composition can include (e.g., naturally or via supplementation) one or more antimicrobial agents and/or other drugs, including those discussed in more detail below.

A curing agent can be used, in certain embodiments, to initiate polymerization, cross-linking, and/or other reactions involving the fibrin and/or fibrinogen within the liquid-containing composition. In some embodiments, the curing agent is pre-loaded into the chamber prior to adding the liquid-containing composition. The curing agent might also be added directly to the liquid-containing composition, in addition to or in place of pre-loading the chamber with the curing agent. A variety of curing agents can be employed. For example, in some embodiments, the curing agent comprises thrombin. The curing agent can comprise a calcium-containing compound (e.g., compounds containing calcium ions), in place of or in addition to other curing agent components. Exemplary calcium ion-containing compounds include calcium salts such as calcium chloride ($CaCl_2$). In certain embodiments, the fibrinogen and/or fibrin are allowed to polymerize and/or cross-link at least partially once they have been exposed to the curing agent (e.g., thrombin, $CaCl_2$, etc.) prior to application of the compressive force.

In some embodiments, a compressive force is applied to the liquid-containing composition, and the fibrin and/or fibrinogen are retained on a filter such that a relatively high concentration of fibrin and/or fibrinogen is present within the concentrated patch. In FIGS. 1A-1C, for example, the liquid-containing composition can be subject to a compressive force by actuating stopper 119 by hand (e.g., by employing a level of force sufficiently high to eject water or other non-patch liquids through filter 116). In certain embodiments, after the compressive force has been applied, the sum of the concentration of the fibrin in the solid matrix and the concentration of the fibrinogen within the matrix is at least about 10, at least about 25, at least about 50, at least about 100, or between about 10 and about 150 grams per liter of the solid matrix. In some embodiments, after the compressive force has been applied, the concentration of the fibrin in the solid matrix is at least about 10, at least about 25, at least about 50, at least about 100, or between about 10 and about 150 grams per liter of the matrix.

The concentration of fibrin within the tissue patch can be increased, in certain embodiments, by causing the fibrinogen within the liquid-containing composition to polymerize to a large degree before and/or during (and, in certain cases, after) application of the compressive force. In certain embodiments, a relatively large portion of the fibrinogen in the liquid-containing composition can be reacted to form fibrin such that the ratio of fibrin to fibrinogen in the tissue patch is relatively high. For example, in some embodiments, the polymerization of the fibrinogen continues until a ratio of an amount of fibrin in the matrix to an amount of fibrinogen in the matrix is at least about 2:1, at least about 5:1, at least about 10:1, or at least about 100:1, by weight.

In some embodiments, the solid matrix can contain relatively highly cross-linked fibrin. Highly cross-linked fibrin can be achieved, for example, by including a cross-linking agent (e.g., thrombin, Factor XIII, calcium-containing compounds, and the like) in the liquid medium to which a compressive force is applied. The degree of cross-linking can be controlled, in certain embodiments, by adjusting the amount(s) of the cross-linking agent(s) present in the liquid medium.

One of ordinary skill in the art would be capable of determining the amount of cross-linking in a given fibrin-containing medium by using one exemplary screening test in which the fibrin-containing medium is submerged in an aqueous solution of 8 molar (i.e., 8M) urea and maintained at a temperature of 25° C. Under such conditions, samples containing highly cross-linked fibrin can take a relatively long time to dissolve, while samples containing slightly cross-linked fibrin (or fibrin that is not cross-linked at all) can be dissolved relatively quickly. In certain embodiments, upon submerging the fibrin-containing portion of the tissue patch in an 8M aqueous solution of urea at 25° C., the fibrin-containing portion will retain its structural integrity (i.e., less than 50 wt % of the portion will dissociate) over a period of at least about 2 hours, at least about 8 hours, at least about 24 hours, at least about 48 hours, at least about 72 hours, at least about 1 week, or at least about 1 month (and/or, up to about 1 year, or longer). In certain embodiments, upon submerging the fibrin-containing portion of the tissue patch in a 6M aqueous solution of urea at 25° C., the fibrin-containing portion will retain its structural integrity (i.e., less than 50 wt % of the portion will dissociate) over a period of at least about 2 hours, at least about 8 hours, at least about 24 hours, at least about 48 hours, at least about 72 hours, at least about 1 week, or at least about 1 month (and/or, up to about 1 year, or longer).

Of course, the tissue patches described herein can also be designed to include fibrin that is cross-linked to a less substantial degree, and in some cases, to include fibrin that is not cross-linked. In certain embodiments, the conditions under which the patch is formed can be selected such that the final patch includes the desired degree of cross-linking, for example, by adding an appropriate amount of cross-linking agent to the liquid medium to which a compressive force is to be applied.

In certain embodiments, the tissue patches can exhibit relatively high tensile strength. Not wishing to be bound by any particular theory, the high tensile strength may result from the relatively high concentration of cross-linked fibrin in the final patch.

Figure 2A:
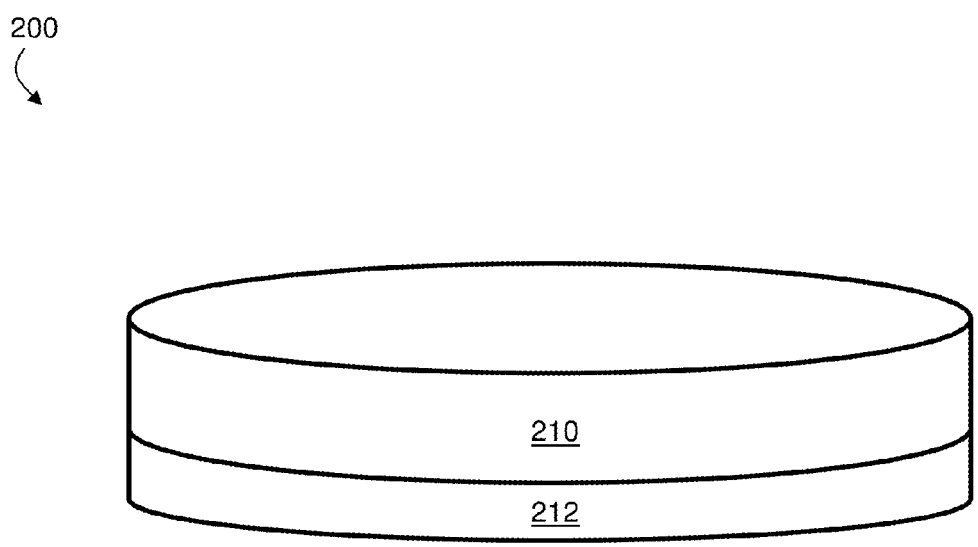
FIG. 2A is, according to certain embodiments, a perspective view schematic illustration of a tissue patch.

After the compressive force has been applied to the liquid-containing composition, a solid matrix can be formed. The solid matrix can comprise polymerized and/or cross-linked fibrin and/or fibrinogen and can be used, for example, as a tissue-adherent patch. FIG. 2A is a schematic, perspective-view illustration of an exemplary patch 200 comprising a solid matrix 210 comprising fibrin and/or fibrinogen. Solid matrix 210 can be fabricated using the systems and methods described above. As illustrated in FIG. 2A, solid matrix 210 is in the form of a cylindrical disc with a substantially circular cross-sectional geometry. In other embodiments, the solid matrix (or the entire tissue patch) can have other cross-sectional geometries such as, for example, substantially elliptical, polygonal (e.g., including any number of sides such as in the form of a triangle, a quadrilateral (e.g., rectangular or substantially square), etc.), irregularly-shaped, or any other suitable shape. The cross-sectional shape of the solid matrix and/or tissue patch can correspond to the cross-sectional shape of the chamber in which it is formed, in certain embodiments. In other embodiments, the solid matrix can be cut or otherwise shaped to assume a geometry that is different than the cross-sectional shape of the chamber in which it is formed.

In certain embodiments, the solid matrix can be unsupported. Generally, unsupported solid matrix materials are those that are able to substantially retain their shape outside a container without the use of a reinforcement structure (e.g., a mesh or other reinforcement structure) within the volume of the solid matrix material. Such materials can also be referred to as self-supporting materials.

In some embodiments, the solid matrix and/or patch can be in the form of a sheet or film. For example, the solid matrix and/or patch may have an aspect ratio (measured as the ratio of the maximum cross-sectional dimension to the minimum thickness of the patch, for example, upon inspection) of at least about 5:1, at least about 10:1, between about 5:1 and about 100:1, or between about 5:1 and about 50:1. In certain embodiments, the solid matrix and/or patch has an average thickness of between about 500 microns and about 1 cm. The average thickness of a component can be determined by measuring the thickness of the patch at a representative number of locations and number averaging the results. In certain embodiments, the solid matrix and/or tissue patch has at least one cross-sectional dimension of at least about 1 cm, at least about 10 cm, at least about 50 cm, or greater. As one particular example, the solid matrix comprises a disc (e.g., a substantially cylindrical disc) with a thickness of between about 500 microns and about 1 cm, and a maximum cross-sectional diameter orthogonal to the thickness that is at least about 1 cm, at least about 10 cm, at least about 50 cm, or greater.

In certain embodiments, patch 200 can include an optional primer region. For example, primer region 212 positioned below solid matrix 210 in FIG. 2A. The patch can be configured to be applied to tissue, in certain embodiments, such that the primer region contacts the tissue. As illustrated in FIG. 2A, primer region 212 and solid matrix 210 are in direct contact. This configuration can be achieved, for example, by applying primer material directly to the solid matrix. The invention is not so limited, however, and in other embodiments, one or more other materials may be positioned between solid matrix 210 and primer region 212.

Primer region 212 can be applied to or otherwise associated with solid matrix 210 via a variety of methods. For example, primer region 212 could be sprayed, brushed, or otherwise applied to solid matrix 210 or an overlying component thereof. In certain embodiments, primer region 212 can be applied to the side of the patch to be applied to a tissue surface in use (e.g., via spraying, brushing, or by any other suitable method), after which solid matrix 210 can be applied over the primer region. In certain instances, a second portion of primer can be applied, for example to the opposite side of the solid matrix as the first application of primer. As one particular example, after applying the solid matrix 210 to a tissue site, additional primer can be applied to the solid matrix and underlying primer.

Primer region 212 can be configured to enhance the degree to which solid matrix 210 is immobilized on a tissue surface. In certain embodiments, the primer region can be selected or configured such that it does not form covalent chemical bonds with tissue. In certain embodiments, the primer region can be selected or configured to interact with tissue via van der Waals forces. For example, the primer region can interact with tissue via physisorption (sometimes also referred to as adhesive dispersion). Examples of potentially suitable primers include, but are not limited to, natural or synthetic resins, zinc-containing materials (e.g., a zinc oxide, a zinc chloride, zinc acetate, zinc stearate, and/or a zinc citrate), metal oxides (e.g., a suspension of metal oxide(s), such as a zinc oxide suspension), metalloid oxides (e.g., a suspension of metalloid oxide(s), such as a silicon oxide suspension), and the like. Such adhesives can be advantageous in part because, while they effectively immobilize the patch on the tissue, they do not form strong (or permanent) bonds, which can lead to tissue damage.

In certain cases, the primer region is configured to immobilize the patch (e.g., by anchoring the patch to the tissue to which it is applied) and provide support while fibrinogen and/or fibrin from the tissue integrates with the fibrin and/or fibrinogen within the solid matrix of the patch. For example, fibrinogen and/or fibrin within the tissue can migrate from the tissue, through the primer, and into the solid matrix of the patch, where the fibrinogen and/or fibrin can polymerize and/or cross-link with fibrinogen and/or fibrin within the solid medium. The integration of the fibrin and/or fibrinogen within a subject's tissue with the fibrin and/or fibrinogen within the patch can lead to the formation of a more robust interface and/or integration region between the tissue and the tissue patch, which can produce enhanced tissue repair.

In certain embodiments, the primer comprises water-activated polymeric adhesive. Those of ordinary skill in the art are familiar with water-activated polymeric adhesives, which are dry adhesive polymeric materials that are rendered tacky by application of water. One can use a water-activated polymeric adhesive by applying water just prior to use, or by relying on water at the application site, to render the adhesive tacky. In certain embodiments, the water-activated adhesive comprises a gum, a resin, or a gel.

The water-activated polymeric adhesive can comprise a vinyl group, in certain embodiments. In certain embodiments, the water-activated polymeric adhesive comprises a co-polymer. For example, the co-polymer can be a co-polymer of a vinyl ether and maleic anhydride. In certain embodiments, the vinyl ether can comprise an alkyl vinyl ether, such that the water-activated polymeric adhesive comprises a co-polymer of an alkyl vinyl ether and maleic anhydride. The alkyl group in the alkyl vinyl ether can comprise an alkyl group containing from 1 to 18 carbons. Examples of such alkyl vinyl ethers include methyl vinyl ether, ethyl vinyl ether, propyl vinyl ether, and isobutyl vinyl ether. In certain embodiments, the vinyl ether in the co-polymer can be a divinyl ether. In certain embodiments, which can be preferred for certain applications, the water-activated polymeric adhesive comprises a co-polymer of methylvinyl ether and maleic anhydride. For example, the primer can comprise Gantrez MS-95.

In some embodiments, the water-activated polymeric adhesive comprising a vinyl group comprises polyvinylpyrrolidone. For example, the water-activated polymeric adhesive can comprise Kollidon®. The water-activated polymeric adhesive comprising a vinyl group can comprise, in some embodiments, a co-polymer of vinyl acetate and polyvinylpyrrolidone. For example, the water-activated polymeric adhesive can comprise, in certain embodiments, Plasdone® S-630.

In some embodiments, the water-activated polymeric adhesive comprises one or more polymers of acrylic acid cross-linked with polyalkenyl ethers and/or divinyl alcohol. For example, the water-activated polymeric adhesive can comprise a Carbopol® polymer.

In certain embodiments, the water-activated polymeric adhesive (which can contain one or more of the water-activated polymeric adhesives described above) is present within the primer in an amount of from about 5 wt % to about 50 wt %, from about 20 wt % to about 40 wt %, from about 25 wt % to about 35 wt %, or from about 30 wt % to about 32 wt %. For example, in certain embodiments, a co-polymer of methylvinyl ether and maleic anhydride is present within the primer in an amount of from about 5 wt % to about 50 wt %, from about 20 wt % to about 40 wt %, from about 25 wt % to about 35 wt %, or from about 30 wt % to about 32 wt %. The water-activated polymeric adhesive can be used as both a bioadhesive and an extended release matrix, in certain embodiments.

The primer comprises, in some embodiments, a cellulose derivative. The cellulose derivative may comprise a cellulose-based polymer substituted with one or more types of functional groups, including alkyl, aryl, heteroalkyl, heteroaryl, heterocycle, carbonyl, halo, hydroxyl, nitro, sulfo, cyano, alcohol groups, combinations thereof, and the like. In some embodiments, the cellulose derivative is a carboxyalkyl cellulose. Examples of suitable cellulose derivatives include, but are not limited to, carboxymethylcellulose (CMC), methylcarboxymethyl cellulose (MCMC), hydroxyethylcarboxymethyl cellulose (HECMC), hydroxyethylmethylcarboxymethylcellulose (HEMCMC), sulfoethylcarboxymethyl cellulose (SECMC), hydroxyethylhydroxypropyl cellulose (HEHPC), hydroxyethylethyl cellulose (HEEC), hydroxyethylsulfoethyl cellulose (HESEC), hydroxypropyl methylcellulose (HPMC), hydroxyethylcellulose (HEC), hydroxypropylcellulose (HPC), hydroxyethylmethylcellulose (HEMC), hydroxyethylmethylcellulose (HEMC), methylcellulose (MC), or combinations of these. In certain embodiments, the cellulose derivative is present within the primer in an amount of from about 1 wt % to about 40 wt %, from about 10 wt % to about 30 wt %, from about 25 wt % to about 25 wt %, from about 20 wt % to about 25 wt %, or from about 21 wt % to about 23 wt %. In certain embodiments, the amount of cellulose derivative included in the primer region can be adjusted to control the viscosity of the primer.

In some embodiments, the primer comprises an oil. In certain embodiments, the oil can comprise a hydrocarbon with a chain length of between about 10 and about 40 carbons, or between about 15 and about 30 carbons. Examples of suitable oils include, but are not limited to, mineral oil, petroleum jelly (e.g., Vaseline®), eugenol, peppermint oil, seed oil, olive oil, or combinations of these. In certain embodiments, the oil component is present within the primer in an amount of from about 3 wt % to about 70 wt %, from about 30 wt % to about 60 wt %, from about 40 wt % to about 50 wt %, or from about 44 wt % to about 48 wt %. In certain embodiments, mineral oil, eugenol, peppermint oil, seed oil, and olive oil are present within the primer such that the combination of these oils is present in an amount of from about 1 wt % to about 50 wt %, from about 15 wt % to about 35 wt %, from about 20 wt % to about 30 wt %, from about 22 wt % to about 28 wt %, or from about 23 wt % to about 25 wt %. In certain embodiments, mineral oil can be present within the primer in an amount of from about 1 wt % to about 50 wt %, from about 15 wt % to about 35 wt %, from about 20 wt % to about 30 wt %, from about 22 wt % to about 28 wt %, or from about 23 wt % to about 25 wt %. In certain embodiments, the primer comprises petroleum jelly (e.g., white petroleum jelly). In some embodiments, the petroleum jelly is present within the primer in an amount of from about 3 wt % to about 70 wt %, from about 10 wt % to about 30 wt %, from about 25 wt % to about 25 wt %, from about 20 wt % to about 25 wt %, or from about 21 wt % to about 23 wt %.

The oils in the primer can be useful for a variety of reasons. First, the oils can act as emollients that provide both a wetting agent and moisture control. Second, the oils can provide a hydrocarbon source which can provide for a "plasticization" source between the primer and the solid matrix (e.g., matrix 210 in FIG. 2A). In some cases, the primer may include a surfactant. It should be noted that the primer is a carefully selected reagent list that contains both water soluble and water swelling materials as well as wetting agents that will allow uniform spreading at the interface of the dressing and the wound site.

The primer may optionally include a metal-containing species and/or a metalloid-containing species, including metals, metal oxides, metalloid oxides, organometallic compounds, and the like. In some embodiments, the primer comprises a metalloid oxide, such as a silicon oxide (e.g., silica) or an aluminum oxide (e.g., alumina) In certain embodiments, the metalloid oxide is present within the primer in an amount of from about 0.1 wt % to about 1 wt % or from about 0.4 wt % to about 0.6 wt %. In some embodiments, a silicon oxide is present within the primer in an amount of from about 0.1 wt % to about 1 wt % or from about 0.4 wt % to about 0.6 wt %. In some embodiments, the primer comprises a metal oxide, such as a zinc oxide. In certain embodiments, the metal oxide is present within the primer in an amount of from about 0.01 wt % to about 0.2 wt % or from about 0.05 wt % to about 0.15 wt %. In some embodiments, zinc oxide is present within the primer in an amount of from about 0.01 wt % to about 0.2 wt % or from about 0.05 wt % to about 0.15 wt %.

The primer can comprise a combination of the above-mentioned components, in some embodiments. For example, in certain embodiments, the primer comprises a combination of at least two of (and, in certain embodiments, all of) a co-polymer of methylvinyl ether and maleic anhydride (e.g., Gantrez MS-95), a cellulose derivative (e.g., carboxymethylcellulose), an oil (e.g., mineral oil), petroleum jelly (e.g., white petroleum jelly), a metalloid oxide (e.g., silica), and a metal oxide (e.g., zinc oxide). These components can be present in any of the weight percentages outlined above. When components are combined in this way, the polymethyl vinyl ether/maleic anhydride co-polymer can serve as a time-dependent dispersant of the petroleum jelly. Petroleum jelly is water insoluble, and could be a potential source of concern for prolonged contact to the wound site. However, degradation of the petroleum jelly can be achieved by the dispersant properties of the polyvinyl methyl ether co-maleic anhydride. Not wishing to be bound by any particular theory, it is believed that the petroleum jelly, which by itself is water insoluble, becomes broken up over time by the dispersant properties of the co-polymer.

In one set of embodiments, the primer comprises a suspension including a relatively high amount of zinc oxide (e.g., optionally in combination with an oil). It has been discovered, within the context of the invention, that primers comprising zinc (e.g., including suspensions of zinc-containing materials (e.g., zinc oxide(s)) such as pastes and creams) can be particularly useful in immobilizing tissue patches on tissue surfaces. In certain embodiments, the primer can include eugenol (in place of or in addition to the zinc-containing component) or other oils, such as mineral oil, Vaseline®, peppermint oil, seed oil, or olive oil. Eugenol is known to those of ordinary skill in the art, and is an allyl chain-substituted guaiacol (2-methoxyphenol). Eugenol generally appears as a clear or pale yellow oily liquid. Eugenol can be derived, for example, clove oil. Besides cloves, it can also be extracted from cinnamon and other aromatic spices. Generally, eugenol is slightly soluble in water and soluble in organic solvents. Eugenol can be used, for example, to make zinc-oxide eugenol paste for temporary fillings in dental applications.

In certain embodiments, the primer region includes the zinc-containing compound (e.g., zinc oxide) in an amount of from about 50 wt % to about 70 wt %. In certain embodiments, the primer region includes the oil compound (e.g., eugenol) in an amount of from about 5 wt % to about 15 wt %, or in an amount of from about 8 wt % to about 12 wt %.

Not wishing to be bound by any particular theory, it is believed that the zinc-containing material (e.g., zinc oxide), optionally with eugenol, forms an anchor site to which the patch becomes "pasted" into position. It is believed that the zinc and the fibrin and/or fibrinogen within the patch interact to impart beneficial strength and elasticity properties to the combination patch and primer (e.g., increasing the tensile strength and elasticity of the patch). In instances where eugenol is employed, it is believed that zinc oxide might react with eugenol to form zinc eugenolate. In certain embodiments in which zinc oxide and eugenol are employed in the primer region, when the zinc oxide and eugenol are exposed to water within the tissue and/or blood, hydrolysis of the zinc eugenolate can occur. The hydrolysis reaction can yield eugenol and zinc hydroxide. The presence of zinc-containing materials such as zinc oxides can also impart desirable antimicrobial properties, as discussed in more detail below.

In certain embodiments, zinc oxide is present in excess such that substantially all of the eugenol reacts and the excess zinc oxide is embedded within the zinc eugenolate matrix. The interlocking zinc oxide eugenolate might give rise to the strength of the paste material Zinc-oxide eugenol paste can include grains of zinc oxide embedded in a zinc eugenolate matrix. In many cases, separate zinc eugenolate units are held together by van der Waals forces and/or particle interlocking. In some such cases, the zinc-oxide eugenol pastes are mechanically weak. However, the weak interaction can be sufficient to immobilize the tissue patches described herein when they are placed on or within tissue sites. In many embodiments, zinc oxide eugenol forms an elastic paste. The elasticity of the paste can allow one to fit the paste into a wound site or other irregularly-shaped space on or within tissue.

It has also been discovered, within the context of the invention, that primers comprising resins can be particularly useful in immobilizing tissue patches on tissue surfaces. In some embodiments, the primer comprises a compound of the general formula $C_xH_yO_z$, wherein x is any integer from 10 to 40, from 15 to 25, or from 18 to 22; y is any integer from 20 to 45 or from 28 to 36; and/or z is any integer from 1 to 5, from 1 to 3, or from 1 to 2. In certain embodiments, the compound may include one or more moieties containing one or more hetero atoms. In some embodiments, the resin comprises at least one aromatic ring, and, in some embodiments, comprises at least 2 or at least 3 fused rings. The resin comprises, in certain embodiments, at least one carboxylic acid group, optionally with at least one carbon-carbon double bond. In certain embodiments, the primer comprises one or more resin acid, such as, for example, abietic acid, plicatic acid, and/or pimaric acid.

In certain particularly advantageous embodiments, the primer region comprises a naturally-derived resin, for example one obtained from a tree, such as pine rosin. It has been unexpectedly found that the use of pine rosin is particularly advantageous as it allows for very effective immobilization of the patch and integration with underlying tissue, even when substantially no compressive force is applied to the patch after it is applied to the tissue site.

Other examples of resins or gums that may be employed in the primer include, but are not limited to, chitosan, sodium alginate, karaya gum, xanthan gum, locust bean gum, guar gum, and pectin.

While non-covalently bound primers have been primarily described, it should be understood that the invention is not limited to the use of such primers, and in other cases, primers that covalently bond to tissue can be employed.

As noted above, in certain embodiments, the tissue patches described herein can have relatively high tensile strengths. In some embodiments, the patch has a tensile strength of at least about 175 kPa, at least about 250 kPa, at least about 500 kPa, at least about 600 kPa, or between about 175 kPa and about 650 kPa, when measured as a true stress at break. In certain embodiments, the solid matrix portion (e.g., 210 in FIG. 2A) of the tissue patch can have a tensile strength of at least about 175 kPa, at least about 250 kPa, at least about 500 kPa, at least about 600 kPa, or between about 175 kPa and about 650 kPa, when measured as a true stress at break. In some embodiments, the combination of the solid matrix portion (e.g., 210 in FIG. 2A) and the primer portion (e.g., 212 in FIG. 2A) can have a tensile strength of at least about 175 kPa, at least about 250 kPa, at least about 500 kPa, at least about 600 kPa, or between about 175 kPa and about 650 kPa, when measured as a true stress at break.

In some embodiments, the tissue patches described herein can be sterilized. For example, the tissue patches can be sterilized using gamma radiation. In certain embodiments, the solid matrix component of the tissue patch can maintain its strength and/or flexibility after sterilization. For example, in some embodiments, the solid matrix material (e.g., material 210 in FIGS. 2A-2D) has a Young's modulus of about 10 GPa or less, of about 1 GPa or less, or of about 100 kPa or less after sterilization using gamma radiation at an intensity of 30 kGy. In some embodiments, the matrix material has a Young's modulus of from about 1 kPa to about 10 GPa, of from about 1 kPa to about 1 GPa, or of from about 1 kPa to about 100 kPa after sterilization using gamma radiation at an intensity of 30 kGy.

In certain embodiments, thrombin can be included on or added to the patch to improve the degree to which the patch adheres to underlying tissue. Not wishing to be bound by any particular theory, it is believed that including thrombin on or within the patch can accelerate the "clot reaction," in which the fibrin from the bleeding subject crosslinks with the fibrin in the patch. It is believed that, by adding thrombin, the clot reaction can be accelerated such that it takes place over a period of time on the order of seconds (e.g., a few seconds or faster), rather than over a period of time on the order of minutes (e.g., up to 10 minutes without the addition of thrombin).

In some embodiments, thrombin can be included within primer region 212, applied to a surface of primer region 212, and/or applied to a surface of solid matrix 210. Thrombin can be, for example, mixed with the primer region material such that it is dispersed within the primer region. In certain embodiments, the thrombin can be applied to an external surface of the solid matrix and/or primer region in the form of a topical solution. Optionally, the topical solution has a thrombin concentration of from about 1 micromolar to about 10 millimolar. In certain embodiments, thrombin can be applied to an external surface of the solid matrix in the form of a powder (e.g., as lyophilized thrombin). Once applied to an external surface, the thrombin can, in certain embodiments, diffuse or otherwise be transported into the bulk of the patch (e.g., into the bulk of solid matrix 210 and/or primer region 212). Thrombin that has been transported to the bulk of the patch can participate in the clot reaction such that the clot reaction occurs both at the surface of the patch as well as within the bulk of the patch.

In some embodiments, a pharmaceutically active composition, growth factor, or other bioactive composition can be applied to a surface of and/or included within the bulk of one or more regions of the patch (e.g., solid matrix 210 and/or primer region 212). In certain embodiments, one or more pharmaceutically active compositions can be included within and/or on a surface of the tissues patches described herein. In some such embodiments, the tissue patch can act as a delivery mechanism for the pharmaceutically active composition. Exemplary pharmaceutically active compositions that be used in association with the tissue patches described herein include, but are not limited to, analgesics, antimicrobial agents (e.g., antibiotics, antifungal, and/or antiviral agents), hormones, insulin, vitamins, and the like. In certain embodiments, the pharmaceutically active composition comprises a small molecule (i.e., a molecule with a molecular weight of less than about 2000 g/mole and, in some instances, less than about 1000 g/mole or less than about 500 g/mole). Exemplary small molecules include, for example, nucleic acids, peptides, polypeptides, peptide nucleic acids, peptidomimetics, carbohydrates, lipids or other organic (carbon containing) or inorganic molecules. In certain embodiments, the pharmaceutically active composition is selected from "Approved Drug Products with Therapeutic Equivalence and Evaluations," published by the United States Food and Drug Administration (F.D.A.) (the "Orange Book").

In certain embodiments, an antimicrobial agent can be applied to a surface of and/or included within the bulk of one or more regions of the patch. The use of antimicrobial agents or other drugs can be advantageous for a variety of reasons. For example, a growing concern with the use of certain tissue sealants is that the tissue sealant can capture or contain bacteria within or under the surface of the tissue sealant and create an environment in which bacteria can grow. Including an antimicrobial agent within one or more surfaces or volumes of the tissue patch can help to combat the growth of bacteria on or around the site to which the tissue patch is applied.

A variety of antimicrobial agents can be incorporated into the tissue patch. The antimicrobial agent may be bacteriocidal, virucidal, fungicidal, and/or any combination thereof. In certain embodiments, a zinc-containing material such as a zinc oxide can be used as an antimicrobial agent. Examples of suitable antimicrobial agents that can be used in association with the tissue patches described herein include, but are not limited to, metal-containing compounds (e.g., zinc-containing compounds, silver-containing compounds (e.g., silver nitrate, silver sulfadiazine, silver foams, flammacerium, Acticoat 7, Aquacel-Ag, Silvercel, and/or silver amniotic membrane), gold-containing compounds, copper-containing compounds, tin-containing compounds, chromium-containing compounds, and the like), organic antimicrobial compounds (e.g., organic antibiotics such as tetracycline antibiotics, rifampin, minocycline, and the like), antimicrobial peptide(s) (e.g., defnsins, histone H1.2, cecropin B, recombinant bactericidal/permeability-increasing protein (rBPI), and/or cer-agenins), chitosan, topical antibiotics (e.g., mafenide acetate, bacitracin, mupirocin, Neosporin®, polymyxin B, nitrofurazone, and/or nystatin), iodine-based compounds (e.g., povidone-iodine, cadexomer iodine, liposomal iodine, and/or Repithel®, and/or Iocide™), and the like. Other agents that can be added to the tissue patches described herein include chlorhexidine, superoxidized water, acidified nitrite, p38MAPK inhibitor, probiotic Lactobacillus, honey, essential oils, and/or papaya.

In some embodiments, one or more growth factors can be included in and/or on a surface of the tissue patches described herein. Such growth factors can contribute to hemostasis, tissue healing, or other biological processes. For example, in certain embodiments, Platelet Derived Growth Factor (PDGF) can be included within and/or on a surface of a tissue patch (e.g., in or on primer region 212, in or on solid matrix 210, or both), which can assist in wound healing. Other examples of growth factors that be included in or on a surface of the tissue patches described herein include, but are not limited to, growth factors from one or more of the following families: adrenomedullin (AM), angiopoietin (Ang), autocrine motility factor, bone morphogenetic proteins (BMPs), brain-derived neurotrophic factor (BDNF), epidermal growth factor (EGF), erythropoietin (EPO), fibroblast growth factor (FGF), glial cell line-derived neurotrophic factor (GDNF), granulocyte colony-stimulating factor (G-CSF), granulocyte macrophage colony-stimulating factor (GM-CSF), growth differentiation factor-9 (GDF9), hepatocyte growth factor (HGF), hepatoma-derived growth factor (HDGF), insulin-like growth factor (IGF), migration-stimulating factor, myostatin (GDF-8), nerve growth factor (NGF) and other neurotrophins, thrombopoietin (TPO), transforming growth factor alpha (TGF-α), transforming growth factor beta (TGF-β), tumor necrosis factor-alpha (TNF-α), vascular endothelial growth factor (VEGF), placental growth factor (PlGF), and the like.

Figure 2B:
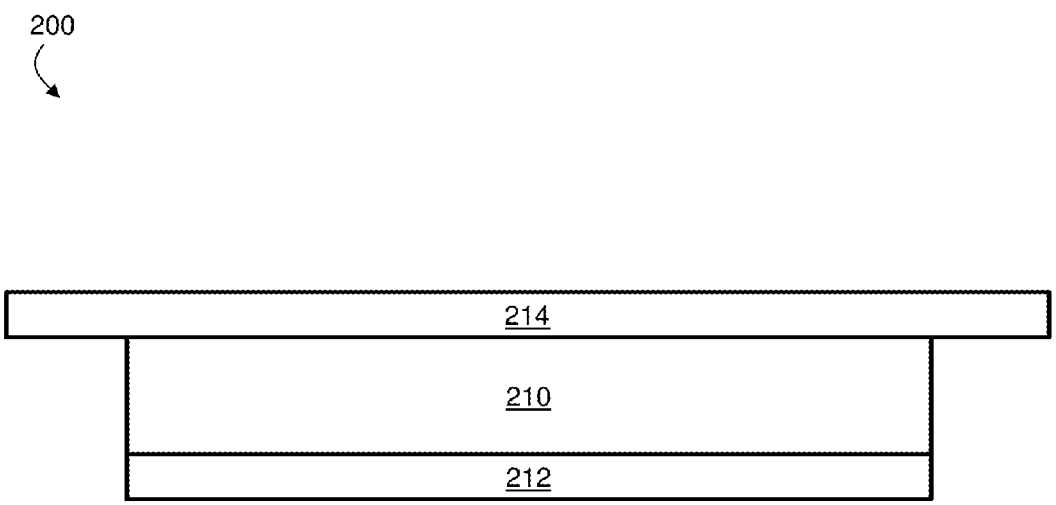
FIG. 2B is a cross-sectional schematic diagram of a tissue patch, according to some embodiments.

In certain embodiments, a backing layer can be applied to the patch. The backing layer can allow one the handle the patch without disrupting the solid matrix layer. The backing layer can be applied to the patch, for example, after the patch has been formed, prior to or after removal from the chamber in which the patch is formed. After the patch has been applied to tissue, the backing layer may, if desired, be removed from the patch, leaving behind an immobilized patch. In FIG. 2B, patch 200 includes optional backing layer 214. Backing layer 214 can be formed of any suitable material. In certain embodiments, the material from which backing layer 214 is formed can be chosen such that the backing layer can be removed from solid matrix 210 without deforming or otherwise disrupting solid matrix 210. The backing layer can comprise, for example, a polymeric film (e.g., comprising polyurethane, silicone, etc.), a cloth-based film, or any other suitable material.

In certain embodiments, a tissue patch can be assembled and used as follows. A solid matrix can be formed by applying a compressive force to a solution containing fibrin and/or fibrinogen within a container such as a syringe. In certain embodiments, the patch can be removed from the syringe and, optionally, a backing layer can be applied to the patch. A primer region (e.g., containing a zinc oxide paste) can be placed on top of the patch, for example, in a thickness of about 1 millimeter. Subsequently, a thrombin topical solution can be applied over the primer region.

Figure 2C:
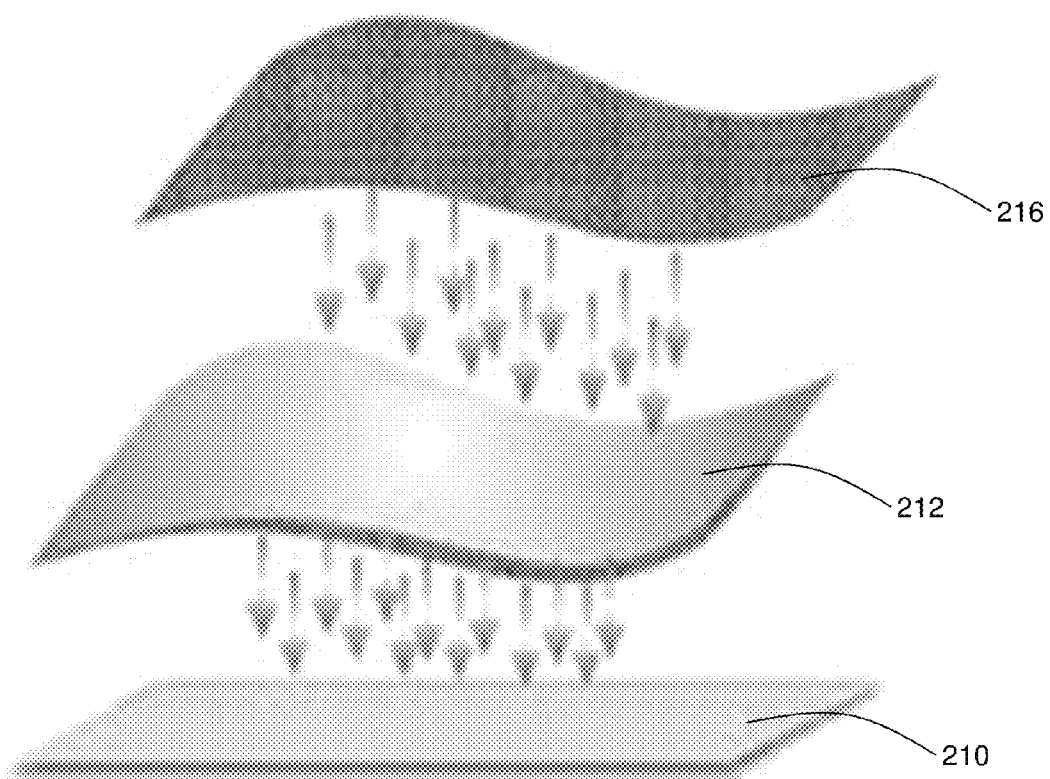
FIG. 2C is a schematic diagram of a tissue patch, according to certain embodiments.
Figure 2D:
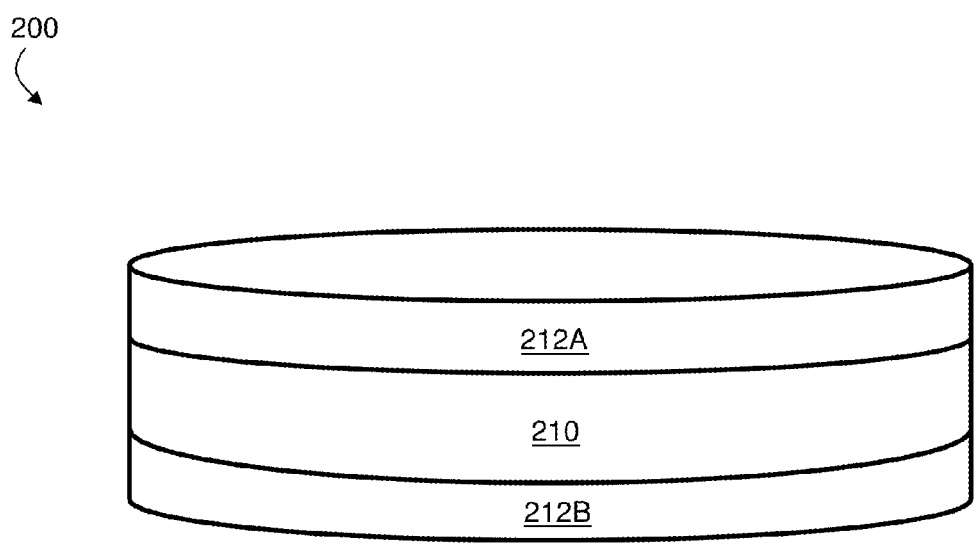
FIG. 2D is a schematic diagram of a tissue patch including primer regions coated on multiple surfaces, according to certain embodiments.

FIG. 2C is a schematic diagram illustrating the assembly of a three-layer tissue patch. Solid matrix 210 can be formed by applying a compressive force to a liquid medium containing fibrin and/or fibrinogen, as described elsewhere herein.

Primer region 212 can be applied over the solid matrix, after which thrombin layer 216 can be applied over primer region 212. Although optional backing layer 214 is not illustrated in FIG. 2C, in certain embodiments, the three-layer tissue patch could also include a backing layer, for example, applied to the side of solid matrix 210 opposite the side over which primer region 212 is arranged. In embodiments in which a separate thrombin layer is employed, the patch can be configured to be applied to tissue such that the thrombin layer contacts the tissue.

In certain embodiments, primer material can be applied to multiple sides of the solid matrix. For example, in FIG. 2D, primer regions 212A and 212B are arranged on opposite sides of solid matrix 210. When arranged in this fashion, the patch can be used to join two surfaces, with a first surface adhering to primer region 212A and a second surface adhering to primer region 212B. Optionally, thrombin can be coated on primer region 212A, on primer region 212B, or on both primer regions 212A and 212B. For example, patches with primer applied on both sides can be used to join two surfaces of skin, a pleural space, spaces between bone tissue surfaces, and other such cavities within a body.

In certain embodiments, the second layer of primer can be applied in situ, rather than before placement of the tissue patch at the wound site. For example, in certain embodiments, a tissue patch with a primer coating on only one side is applied at a tissue site. In certain such embodiments, after the tissue patch has been properly positioned, a second layer of primer is applied over a second portion of the tissue patch that is not in contact with the tissue. After application of the primer to the second portion of the tissue patch, additional tissue can be positioned over the second portion of the tissue patch. Applying the tissue patch in this manner can aid in positioning the second tissue surface over the first tissue surface.

Once applied to a tissue site, blood from the subject can naturally start the coagulation process. The primer region can provide an adhesive anchor material that holds the patch in place over the tissue, even when it is bleeding. The thrombin on and/or in the patch can accelerate the clot reaction such that the time over which the fibrin from the patch crosslinks to the fibrin from the subject is reduced. In this way, the tissue patch works as both a sealant as well as a medium to release and/or deliver thrombin to the tissue site.

One advantage of the procedures outlined herein is that they can be used to quickly and easily produce fibrin-containing tissue patches. In certain embodiments, for example, the liquid-containing composition and initiator (e.g., thrombin) can be allowed to mix for a short period of time (e.g., in some cases for as little as 30 seconds). The step of applying a compressive force can be completed on the order of minutes (and in some cases, in as little as 30 seconds or shorter). In certain embodiments, as soon as the application of the compressive force is completed, the concentrated fibrin and/or fibrinogen material on or near the filter can be removed and used. Accordingly, in certain embodiments, the entire patch fabrication process can be completed in as little as minutes (and in certain cases, in less than 1 minute). For example, in some embodiments in which autologous blood is used to fabricate the patch, the time it takes to fabricate a patch from the time a blood sample is finished being taken to the time the patch is ready for application can be less than about 5 minutes or less than about 1 minute.

The ease with which the tissue patches described herein can be produced can provide flexibility in the way the patches are used. The patches described herein can be produced and applied directly at the site of use, in certain embodiments. For example, in some embodiments, a blood sample can be taken from a subject and added to a patch fabrication system (e.g., such as syringe 100) at the site at which the blood sample was taken. A tissue patch can be produced, removed from the fabrication system, and applied to the subject from which the blood sample was taken. Of course, in other embodiments, the patches can be packaged after production, for application at a later time. For example, a patch can be fabricated using a liquid-containing composition (e.g., blood sample or fibrin solution) sourced from a site remote to the site of the patch production (e.g., from a blood or plasma transfusion center). The liquid-containing composition can be used to produce a patch that is subsequently sterilized and packaged (and optionally stored for days, weeks, months, or longer) for application to a subject at a location remote from the patch production location.

In another aspect, the present invention is directed to a kit including one or more of the components discussed herein. For example, in some embodiments, the kit comprises a syringe (e.g., syringe 100 in FIGS. 1A-1C). The kit can comprise, in certain embodiments, a liquid-containing composition comprising fibrin and/or fibrinogen, such as blood, a plasma component of blood, and/or a solution of fibrin and/or fibrinogen. In some embodiments, the kit comprises a filter (e.g., filter 116 in FIGS. 1A-1C). The filter can be configured, in certain embodiments, to separate fibrin and/or fibrinogen within blood (or within another liquid containing fibrin and/or fibrinogen) from at least one other component of the blood (or from at least one other component of the fibrin- and/or fibrin-containing liquid), as described above. The kit can comprise, in certain embodiments, a curing agent. The curing agent can be capable of activating the polymerization of fibrinogen to fibrin and/or capable of activating the cross-linking of fibrin, as described above. The kit can comprise, in some embodiments, a primer, including, for example, any of the primer materials discussed herein in association with primer region 212. In some embodiments, one or more components of the kit (e.g., the syringe, the filter, the curing agent, the primer, and/or other components of the kit) can be sterile.

In certain embodiments, a kit is provided including a solid matrix comprising fibrin and/or fibrinogen, which can be sterile and configured for application to a tissue surface. The kit can also comprise a primer composition. The primer composition can include any of the ingredients described elsewhere herein. For example, the primer composition can comprise at least one of a water-activated polymeric adhesive, a cellulose derivative, an oil, and a metal-containing species. In certain embodiments, the primer composition in the kit may be kept separate from the solid matrix in the packaging of the kit such that the primer composition has not yet been applied to the solid matrix prior to use.

A "kit," as used herein, typically defines a package or an assembly including one or more of the components of the invention, and/or other components associated with the invention, for example, as previously described. A kit of the invention may, in some cases, include instructions in any form that are provided in connection with the components of the invention in such a manner that one of ordinary skill in the art would recognize that the instructions are to be associated with the components of the invention. For instance, the instructions may include instructions for the use, modification, assembly, storage, or packaging of the components. In certain embodiments, the instructions include instructions for mixing, diluting, preserving, administering, and/or preparing compositions (e.g., blood samples, fibrinogen solutions, and the like) for use in association with the components of the kit. In some cases, the instructions may also include instructions for the use of the components or associated compositions, for example, for a particular use, e.g., to assemble a tissue patch. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

The tissue patches described herein can be used in a wide variety of applications including, for example, general surgery, vascular surgery, spine surgery and ophthalmologic surgery. The tissue patches can be configured to be applied to any type of tissue including soft tissue, bone tissue, or any other type of tissue. Tissue patches can be employed to: assist hemostasis in a bleeding area, reduce blood flow from solid organs, assist in sealing suture holes, assist in sealing anastomosis or leaks from hollow organs, assist or replace sutures in surgical procedures (particularly where suturing is difficult or impossible), produce a water-tight closure across portions of tissue (e.g., across a suture line), reinforce tissue (e.g., in reinforcing suture lines including high stress suture lines), perform of tissue approximation, replace sutures, fill dead space or other voids in tissue, and/or in vascular repair (e.g., to seal a vascular defect). In certain embodiments, tissue patches can be employed to perform gastrointestinal suture line reinforcement, in preventing the formation of seroma (e.g., after surgical procedures), for use as soft tissue (e.g., after breast cancer or other surgical procedures in which tissue may be removed), as burn dressings, and/or for combined hemostasis/sealing and drug delivery.

In some embodiments, the tissue patches can be used to treat spleen tissue, for example, to inhibit or stop bleeding or the leaking of other bodily fluids and/or to partially or completely fill void(s) in the spleen. In certain embodiments, the tissue patches can be used to treat lung tissue, for example, to inhibit or stop bleeding or the leaking of other bodily fluids, to partially or completely fill void(s) in the lung, and/or to inhibit or stop the leaking of air from the internal cavity of a lung. In some embodiments, the tissue patches described herein can be used to treat the liver, for example, to inhibit or stop bleeding or the leaking of other bodily fluids from the liver and/or to partially or completely fill void(s) in the liver. In certain embodiments, the tissue patches can be used to treat heart tissue, for example, to inhibit or stop bleeding or the leaking of other bodily fluids, to partially or completely fill void(s) in the heart or associated blood vessels, and/or to inhibit or stop the leaking of blood from an internal cavity of a heart. The tissue patches described herein can also be used to treat tissues in or near the gastrointestinal tract, for example, to inhibit or stop bleeding or the leaking of other bodily fluids, to partially or completely fill void(s) in gastrointestinal tissues.

The patches described herein can have a variety of advantageous properties. For example, certain embodiments of the fibrin patch can be formed and applied at the site of application. In addition, the production and application process does not require the thrombin induction of clot formation on a bleeding site. Also, the fibrin concentration of some embodiments of the patch greatly exceeds the fibrin concentration that is achieved using many traditional thrombin tissue sealants, where the only fibrin in the end thrombus is what forms at the surface of the bleeding site. Also, as noted above, patches formed according to certain embodiments of the methods described herein can have relatively high tensile strengths. Moreover, some embodiments of the patches described herein are capable of adhering to a wet (e.g., bleeding) tissue surface. Also, certain embodiments of the patches described herein are capable of chemically reacting (e.g., polymerizing and/or cross-linking) with fibrin and/or fibrinogen present at the site of application (e.g., with the fibrin and/or fibrinogen within a subject's tissue).

The tissue patches can be biocompatible and/or biodegradable. In addition, the patches can be configured such that they do not interfere with any metabolic pathways that would produce significant biologic dysfunction. The use of sterile materials and components to form certain embodiments of the patch can reduce or eliminate the risk of bacterial, viral, or other infectious agents being transmitted as the result of the use of the patch.

Certain embodiments of tissue patches described herein can be prepared quickly and easily. For example, in many embodiments, production of the tissue patch can be achieved simply by adding the liquid-containing composition to the chamber (such as a syringe), applying a compressive force to the liquid, and removing the patch from the filter. This process can take as little as minutes, or less, in many embodiments. In addition, the components used to make certain embodiments of the patches can have a relatively long shelf life, especially when enclosed in a sterile package.

The tissue patches described herein can be used to treat human subjects, in certain embodiments. In other embodiments, the tissue patches described herein can be used to treat non-human animal subjects. For example, in certain cases, the tissue patches described herein can be used in veterinary applications, for example, those involving horses, dogs, cats, and the like.

U.S. Provisional Patent Application Ser. No. 61/594,898, filed Feb. 3, 2012, and entitled "Tissue Patches and Associated Systems and Methods" is incorporated herein by reference in its entirety for all purposes. A U.S. Patent Application filed on even date herewith and entitled "Systems and Kits for the Fabrication of Tissue Patches" and a U.S. Patent Application filed on even date herewith and entitled "Systems and Methods for the Fabrication of Tissue Patches" are also incorporated herein by reference in their entirety for all purposes.

The following examples are intended to illustrate certain embodiments of the present invention, but do not exemplify the full scope of the invention.

Example 1

This example describes the production of a tissue patch comprising cross-linked fibrin, fabricated by applying a compressive force to a liquid-containing composition comprising fibrinogen within a syringe. The fabrication process in this example takes advantage of the rapid conversion of fibrinogen into fibrin using thrombin. The patches were made by applying a compressive force to the fibrin-containing medium onto a small surface area disc to produce a high tensile strength patch material, as described below.

Patches were fabricated using both whole blood and a liquid-containing composition comprising purified bovine fibrinogen (Lyophilized Technical Grade Bovine Thrombin, Prod. No. 91-010, BioPharm Laboratories, Bluffdale, Utah). For each patch made, the conversion of fibrinogen to cross-linked fibrin was initiated by adding 300 units of thrombin to 15 mL of plasma. The solution was allowed to sit for 60 seconds, while at least a portion of the fibrinogen was polymerized to form fibrin. 200 microliters of 2 Molar $CaCl_2$ were also added to the plasma to provide additional crosslinking due to the calcium dependency of Factor XIII. It should be noted that the use of $CaCl_2$ is optional, and, in other experiments, sufficient cross-linking was achieved without the use of $CaCl_2$.

10 milliliters of liquid medium was loaded into a 10 milliliter syringe. A rigid disc filter was placed within a filter holder (Swinnex Filter Holder, 25 mm, Catalog Number SX0002500, EMD Millipore Corporation, Billerica, Mass.). The filter holder was attached to the discharge end of the syringe, similar to the arrangement illustrated in FIG. 1C. A disc filter similar to the filter illustrated in FIG. 3A was used. The disc filter was made by forming a plurality of 0.047-inch diameter pores in a 1.5 millimeter thick polyolefin disc.

After loading, a compressive force was applied, by hand, to the liquid-containing composition within the syringe. The amount of pressure used to apply the compressive force to the patch material was substantially the same as the amount of pressure that was typically required to evacuate the syringe when filled with water. The syringe was preloaded with 1000 IU thrombin, which rapidly induced substantially complete clot formation within the syringe. As a compressive force was applied to the liquid media within the syringe, the filter allowed substantially all of the non-gelatinous material (e.g., water) to pass across, but retained and concentrated substantially all of the gelatinous portion.

This process produced 15-millimeter diameter patches concentrated to a thickness of approximately 2 millimeters on the filter disc. Once removed from the disc, the patch was ready to be applied to a bleeding site. Rosin was applied over the patch using a brush applicator. The rosin was obtained from Naturallist located in Stratton, Me.

Figure 3B:
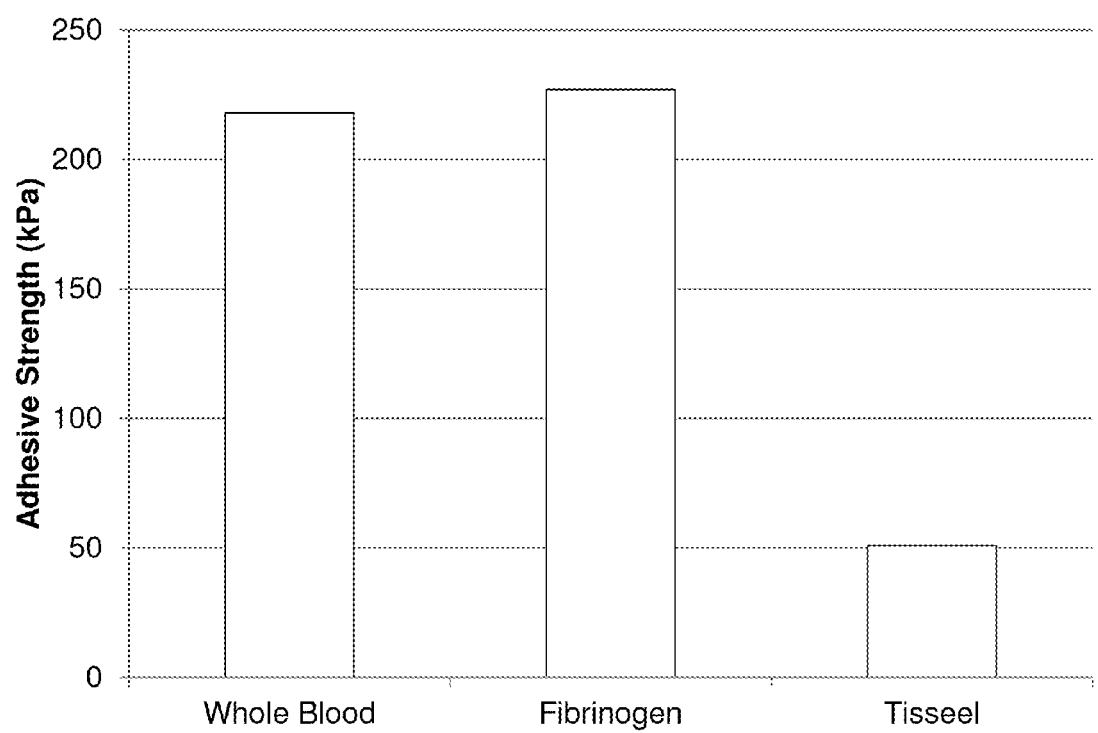
FIG. 3B is an exemplary plot of adhesive strength for a variety of tissue patches and sealants.

The adhesive properties of several patches were assessed following methods described by Elvin (Elvin, et al., "Photochemical fabrication of a highly elastic and adhesive surgical tissue sealant," *European Cells and Materials*, Vol. 20. Suppl. 3, page 71, 2010, ISSN 1473-2262). Briefly, an adhesive resin-coated patch, fabricated as described above, was applied between two pieces of bovine amnion, each stretched over the end of a Perspex cylinder (176 mm$^2$). After application of the patch, the force required to pull the two amniotic membranes apart (at a strain rate of 1 mm/min) was measured on an Instron mechanical tester with a 5 N load cell. As illustrated in FIG. 3B, the mean adhesive strength for the three whole blood patches that were tested was 218 kPa. The mean adhesive strength of the three patches fabricated from purified fibrinogen was 227 kPa. As a comparison, the adhesion strength of commercially available fibrin sealant Tisseel (from Baxter BioSurgery) was also measured as 51 kPa.

The tensile properties of the tissue patches and a patch produced from the commercially-available Tisseel product were also tested. The patch samples were analyzed on an Instron mechanical tester as described by Elvin, noted above. The tested patch had a gauge length of 8 mm and a cross-sectional area of 5 mm$^2$. The patches were strained at a rate of 5 mm/min until failure. The tensile modulus of elasticity was determined from the stress-strain curve as the absolute value of the slope of the secant at 100% strain. The results are shown in Table 1 below.

TABLE 1

Tensile testing results for patches produced in Example 1.

|  | Whole Blood Patch | Fibrinogen Patch | Tisseel |
|---|---|---|---|
| Engineering stress at break (kPa) | 119.4 | 132.6 | 14.3 |
| True Stress at Break (kPa) | 629.4 | 502.7 | 49.2 |
| Extension to break (%) | 181.2 | 147.3 | 23.2 |

Example 2

Patches were evaluated via experiments on a 49.5 kilogram pig following procedures outlined in Browdie, D. A., et al., "Tests of Experimental Tissue Adhesive Sealants, *Texas Heart Institute Journal*, 2007, 34, pp. 313-317. This study was designed to determine if the patch was capable of adhering to a wound site, providing a seal to inhibit leakage, and inhibiting bleeding (i.e., acting as a hemostatic agent). The patches tested in this example were made according to the methods outlined in Example 1, using porcine plasma obtained from Integra Group (Brooklyn Park Minn.) as the source of fibrin and fibrinogen. In this example, in tests in which primer was employed, the primer included zinc oxide paste and eugenol Zinc oxide paste was made by mixing 50 wt % to 70 wt % zinc oxide (Sigma-Aldrich, St Louis, Mo., Catalog #14439-100G) with 10 wt % eugenol (Sigma-Aldrich, St Louis, Mo., Catalog #E51791). Thickeners and other components in water may also be added. The primer was mixed until it formed a viscous paste. In tests in which a thrombin coating was used, a topical solution containing thrombin (bovine thrombin, BioPharm Laboratories, LLC, Bluffdale, Utah, Product Number 91-010) in a concentration of 1300 U was employed.

First, the patches were evaluated as topical sealants on the hind leg of the pig. Using a surgical blade a 20 mm incision was made along a superficial vein on the right leg of the pig. Once a strong bleed was achieved, a 25 mm patch with a 1 mm primer was applied to the incision, and pressure was applied for 30 seconds. After 30 seconds of light pressure the site was observed. A substantially complete seal was achieved in 30 seconds. After 5 minutes of applying the patch, the right hind leg was aggressively manipulated in an attempt to disrupt the patch. The seal held substantially completely.

The patch was also evaluated as a topical sealant on the left superficial mammary vein of a pig. Using a surgical blade, a 20 mm incision was made along the left superficial mammary vein of the pig. Once a very strong bleed was achieved, a 25 mm patch with 1 mm primer was applied and pressure was applied for 30 seconds. After 30 seconds of light pressure, a complete seal was observed at the site. After 5 minutes, the skin area was manipulated in a manner to disrupt the patch, and the patch held with no additional bleeding.

The patch was also evaluated as a sealant for splenic leaking tissue surfaces. Two splenic leaking tissue surfaces were produced by use of an 8 mm biopsy punch in which a punch hole was made in the spleen. The tissue was removed, yielding a steady, aggressive bleed. After the biopsy punch, the a 25 mm patch with 1 mm primer was applied. Light compression was held for 30 seconds. After 30 seconds a heavy bleed continued and pressure was reapplied for 2 minutes. Bleeding continued and complete hemostasis was not achieved. However, using the same biopsy site, a second 25 mm patch with 1 mm primer and a thrombin coating was applied, and light compression was held for two minutes. After two minutes, complete hemostasis was achieved.

A third splenic leaking surface was introduced on the pig using a large knife and scissors to produce amputation laceration injuries at substantially right angles to the long axis of the spleen. This produced leaking tissue surface areas of about 4 cm$^2$ located more than 3 cm from the splenic capsule. A pre-fabricated and refrigerated 25 mm patch with a 1 mm primer region was applied with light compression and held for 30 seconds. Slight bleeding continued after 30 second of pressure, so an additional 90 seconds of pressure was applied. After two minutes, complete hemostasis was achieved.

A fourth splenic leaking surface was produced by making a very deep laceration, which produced an aggressive bleed. The size of the laceration was around 25 mm. A 25 mm patch with a 1 mm primer region and a thrombin coating was applied, and light compression was held for two minutes. After two minutes complete hemostasis was achieved.

Tissue patches were also evaluated as sealants for hepatic leaking tissue surfaces. Leaking tissue surface areas (about 16 cm$^2$ located more than 3 cm from the hepatic capsule) were produced by means of an 8 mm biopsy punch. After strong bleeds were achieved, a 25 mm patch with 1 mm primer and a thrombin coating was applied with light compression, and was held for 60 seconds. After 60 seconds complete hemostasis was achieved.

Patches were also evaluated as sealants for filling the pleura space. In one test, a standard left thoracotomy incision was performed. The incision initially was carried down through the skin, subcutaneous fat and muscle layers. The fifth rib was identified and the intercostal muscle of the 4th intercostal space was divided. The pleura was not incised. The isolated pleura of this space was incised for approximately 1 cm. The area was flooded with saline to demonstrate an air leak by observing bubbling upon inhalation. Thereafter, a patch was applied to the opening in the pleura. The patch was specifically made for this test by using a 25 mm patch with 1 mm primer. A longitudinal tissue patch wedge that was about 3 mm thick was placed on top of the 25 mm patch. The patch was coated with thrombin solution. After applying the patch to the pleura space, light compression was held in place for 2 minutes. Thereafter, the patch was carefully removed, and irrigation fluid was poured over the reparative site, demonstrating a successful sealing of the created pleura opening. Following this experiment, the left thoracotomy was completed.

Tissue patches were also evaluated as sealants for sealing lung punctures. Distal apical resections were initially performed with subsequent applications of a patch containing the surgical adhesive. Prior to applying the patch with the surgical adhesive, bleeding and the presence of air leaks were determined. Following the application of the patch with the surgical adhesive, all created lesions were hemostatic with cessation of air leaks. Next, a puncture wound was created in approximately the mid portion of the upper lobe of the lung using a scalpel. There was obvious bleeding with the presence of air leaks after removal of the scalpel. A patch with surgical adhesive was applied to this puncture wound. The patch with the surgical adhesive was held for approximately 2 minutes. The patch was removed carefully. Hemostasis and cessation of air leaks were determined.

The patches were also evaluated as sealants for sealing an atriotomy. In this test, the pericardium was incised longitudinally. The left atrium was exposed. A purse string suture was placed in the lateral wall of the left atrium. An angiocatheter was inserted into the left atrium at approximately the center of the purse string suture. The suture was tied around the indwelling angiocatheter. The angiocatheter was removed. There was bleeding noted from the left atrium at the insertion site of the angiocatheter. A patch with the surgical adhesive was applied to the bleeding site. The patch was held in place for approximately 2 minutes. The patch was carefully removed, and hemostasis was obtained.

The strength of the lung sealant was also evaluated. 60 minutes after the lung puncture and lung apex were closed, the strength of the seal was evaluated by over inflating the lung. Both patches substantially completely held after lung over-inflation. Pull away tests were performed in which the patch was pulled away from the lung tissue. The patch would not release from the lung. Further force was applied until the lung tissue distal to the patch started to tear; however, the patch remained fully intact.

Example 3

This example describes animal testing of a tissue patch including a primer region comprising Gantrez MS-95 (a co-polymer of methylvinyl ether and maleic anhydride), carboxymethylcellulose, mineral oil, white petroleum jelly, silica, and zinc oxide.

Patches were made by applying primer material and thrombin to a solid matrix containing fibrin and fibrinogen.

To make the solid matrix, 15 mL of porcine plasma was added to a 20 mL slip tip syringe. Using a micropipet, 200 uL of 2M $CaCl_2$ was pipetted into the syringe. Subsequently, 200 uL of 3000 U/mL bovine thrombin was pipetted into the syringe using a micropipet. The syringe was then inverted quickly three times. The syringe was placed in a 37° C. incubator for 15 minutes. A rigid 25-mm patch making filter, made by forming a plurality of 0.047-inch diameter pores in a 1.5 millimeter thick polyolefin disc and similar to the filter illustrated in FIG. 3A, was placed within a filter holder (Swinnex Filter Holder, 25 mm, Catalog Number SX0002500, EMD Millipore Corporation, Billerica, Mass.). The filter holder was attached to the discharge end of the syringe, similar to the arrangement illustrated in FIG. 1C. The contents of the syringe were evacuated across the filter fixture by applying a compressive force by hand. Finally, the holder was unscrewed, and the solid matrix was dislodged from the filter fixture using a gloved finger. The resulting solid matrix had a 25-mm diameter and a thickness of 1 mm.

After the solid matrix had been formed, a primer region was applied to the textured side of the solid matrix (i.e., the side of the solid matrix that was in contact with the filter during fabrication of the matrix). The primer region was made by mixing 31.4 wt % Gantrez MS-95 (a co-polymer of methylvinyl ether and maleic anhydride) (ISP Specialty Chemicals), 22.0 wt % carboxymethylcellulose (Sigma-Aldrich), 24.0 wt % mineral oil (Sigma-Aldrich), 22.0 wt % white petroleum jelly (Vaseline®), 0.5 wt % silica (Sigma-Aldrich), and 0.1 wt % zinc oxide (Sigma-Aldrich). The primer region had a thickness of 1 mm.

After the primer region had been applied, a longitudinal tissue patch wedge that was about 3 mm thick was placed on top of the 25 mm patch. The patch was then coated with 500 IU bovine thrombin (Bovine Thrombin, Prod. No. 91-010, BioPharm Laboratories, Bluffdale, Utah). Specifically, 0.33 g of 100,000 U/gram bovine thrombin was added to 10 mL of sterile water. A 200 microliter volume into was transferred to microfuge tubes and frozen, after which the thrombin was applied to the patch.

Patches fabricated as outlined above were evaluated in porcine model experiments following procedures outlined in Browdie, D. A., et al., "Tests of Experimental Tissue Adhesive Sealants, *Texas Heart Institute Journal*, 2007, 34, pp. 313-317. In a first set of tests, patches were inserted into 8-mm biopsy punches made in a liver and a spleen. The patches successfully stopped bleeding in these wounds.

In a second set of experiments, performance of the patches in sealing the pleura space was analyzed. A standard left thoracotomy incision was performed. The incision was initially carried down through the skin, subcutaneous fat and muscle layers. The fifth rib was identified and the intercostal muscle of the 4th intercostal space was divided. The pleura was not incised. The isolated pleura of this space was incised for approximately 1 cm. The area was flooded with saline to demonstrate an air leak by observing bubbling upon inhalation. After applying the patch to the pleura space, light compression was held in place for two minutes. Thereafter, the patch was carefully removed and irrigation fluid was poured over the reparative site, demonstrating a successful sealing of the created pleura opening. Successful sealing in the air leak model is encouraging for the seroma drainage model due to the fact that the analyzed area had only minor bleeding and the patch was able to seal an area under positive and negative pressure.

Based on the results outlined above, it is anticipated that prevention of seroma drainage using these patches will be straightforward.

Example 4

This example describes experiments in which the cross-linking of the tissue patch is controlled. The tissue patch can be engineered to include any desirable amount of cross-linking, for example, being highly cross-linked, having substantially no cross linking, or having an intermediate amount of cross-linking. Control of cross-linking can be achieved, for example, by controlling the ability of Factor XIII to form covalent bonds between the fibrin strands. A fibrin clot alone has no covalent bonds and is generally readily dissociated in the presence of 8 Molar (i.e., 8 M) urea. A highly crossed clot, in which Factor XIII has formed cross-linkages, will not dissolve in the presence of 8M urea.

Tissue patches were fabricated using 15 mL of citrated porcine plasma. In a first case (Case 1), the porcine plasma was not supplemented with any additive. In a second case (Case 2), the porcine plasma was supplemented with 200 microliters of 2M $CaCl_2$. In a third case (Case 3), the porcine plasma was supplemented with 0.7 mL of 0.1M EDTA. 200 uL of 3000 U/mL bovine thrombin was added to each sample in a syringe. Samples were inverted 2-3 times and allowed to incubate at 37° C. for 10 minutes. Patches were constructed by compressing the clotted plasma over a 50 mm filter assembly, using the methods described in Example 3. Patches were then cut into 1 $cm^2$ squares.

In a fourth set of experiments (Case 4), patches were made according to the examples described in U.S. Pat. No. 2,576,006, to Ferry et al., patented on Nov. 20, 1951.

Each of the patches were exposed to 3 mL of 6 M urea at 25° C. The Case 2 patches remained completely intact after 7 months of exposure to the urea. The Case 1 patches remained completely intact for 24 hours, but were dissolved within 14 days. The Case 3 patches were partially dissolved after 2 hours, and completely dissolved after 24 hours. The Case 4 patches (fabricated according to the methods described in U.S. Pat. No. 2,576,006) were dissolved within 1 hour. It is believed that similar results would be achieved using aqueous solutions of 8 M urea at 25° C.

These experiments demonstrated that the patches fabricated according to the inventive methods described herein can be engineered to include a desired amount of cross-linking, which one might want to tailor to meet the needs of a specific application. These experiments also demonstrate that the patches made according to the methods described in U.S. Pat. No. 2,576,006 are weak compared to the patches described herein. Generally, the patches made according to the methods described in U.S. Pat. No. 2,576,006 have substantially no covalent bonds because Factor XIII is not activated.

Without wishing to be bound by any particular theory, it is believed that Factor XIII is activated by thrombin into factor XIIIa. The activation of Factor XIII into Factor XIIIa requires calcium as a cofactor. Factor XIII is a transglutaminase that circulates in the plasma as a heterotetramer of two catalytic A subunits and two carrier B subunits. When thrombin has converted fibrinogen to fibrin, it is believed that the latter forms a proteinaceous network in which every E-unit is crosslinked to only one D-unit. In the presence of calcium the carrier subunits dissociate from the catalytic subunits, leading to a 3D change in conformation of factor XIII and hence the exposure of catalytic cysteine residue. Upon activation by thrombin, factor XIIIa acts on fibrin to form γ-glutamyl-ε-lysyl amide cross links between fibrin molecules to form an insoluble clot.

Example 5

This example describes the mechanical testing of tissue patches to determine Young's Moduli and other physical properties. The patches were made as follows. Plasma was obtained and brought to room temperature. 15 mL of plasma was added to a 20 mL slip tip syringe. 200 microliters of 2M $CaCl_2$ was pipetted into the syringe using a micropipet. Using a micropipet, 200 uL of 3000 U/mL bovine thrombin was pipetted into the syringe. The syringe was then quickly inverted 3 times. The syringe was then placed in a 37° C. incubator for 15 minutes. A 25-mm patch making filter fixture was then attached to the syringe, and the entire contents of the syringe were evacuated across the filter, as described in Example 3. After evacuation, the filter fixture was removed, and the patch was dislodged from the filter using a gloved finger. Using a scalpel, the samples were manually cut into "dogbone" shapes with a narrow region about 0.25 inches wide and a thickness of about 1 mm.

Samples were tested on an Instron model 58R4505 Mechanical Test System using a 50 N (about 10 pound) loadcell and a crosshead speed of 1.0 inch per minute. Rubber lined pneumatic grips were used with the pressure set at about 20 psi. The gage length and spacing between the jaw grips varied as it was adjusted to the available sample length.

In a first set of tests, the effect of sterilizing the patches using gamma radiation was investigated. Patches were prepared as described above and sent to Steris Corporation for sterilization. Each sample was sealed in a foil pouch and sterilized using gamma radiation from a cobalt radiation source. Samples were sterilized at two different intensities, 30 kGray (i.e., 30 kGy) and 50 kGray. In addition, a control sample, which was not sterilized, was tested.

Figure 4A:
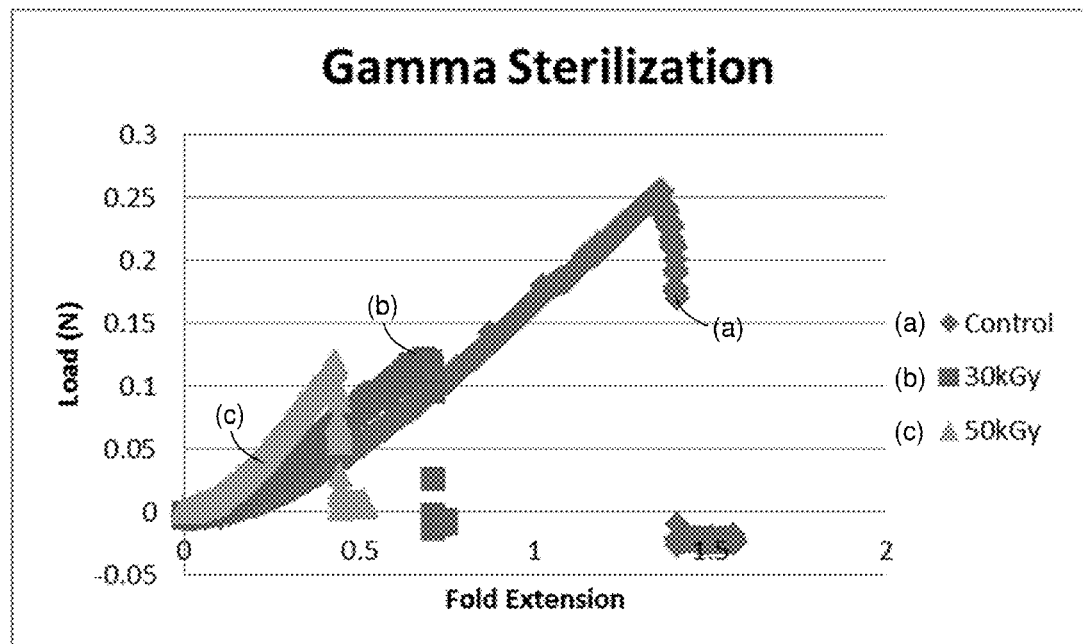
FIGS. 4A-4F are exemplary plots of stress-strain curves illustrating mechanical characteristics of tissue patches, according to certain embodiments.

After sterilization, the samples were tested in the Instron Mechanical Test System, as described above. FIG. 4A includes plots of the stress/strain curves of the tested samples. In FIGS. 4A-4G, the Young's moduli of the tested samples can be calculated as follows:

$$E = \frac{\text{Slope of stress} - \text{strain curve}}{\text{Cross-sectional area of sample}} \quad [1]$$

As noted above, the cross-sectional dimensions of all of the samples tested in this example were 1 mm by 0.25 inches, which translates to a cross-sectional area of about 6.35 $mm^2$. Accordingly, in FIG. 4A, the control and 30 kGy-sterilized samples exhibited Young's moduli of about 35 kPa and the 50 kGy-sterilized sample exhibited a Young's modulus of about 70 kPa. The control sample exhibited the greatest strength and extension, while the 30 kGy-sterilized sample exhibited the second highest strength and extension.

In a separate set of experiments, patches were made according to the procedure described in U.S. Pat. No. 2,576, 006, to Ferry et al. After sterilization at 30 kGy and 50 kGy, the patches were too brittle to be tested and were essentially inelastic.

Figure 4B:
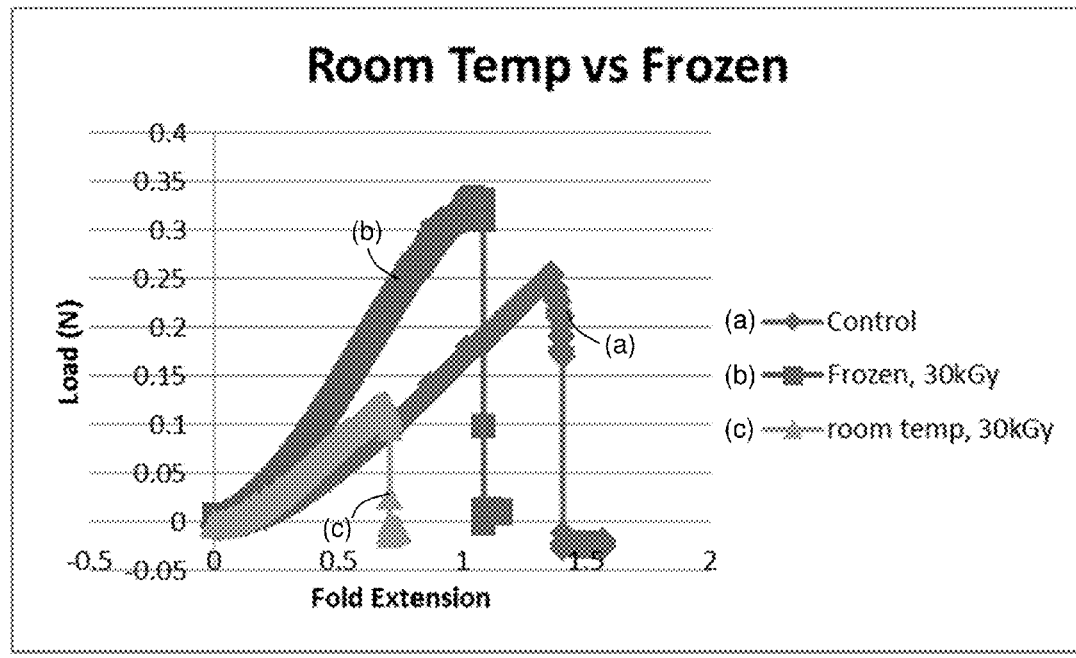

In another set of experiments, the effect of freezing on the mechanical properties of the patches was investigated. One set of samples was frozen using dry ice while another set was kept at room temperature after fabrication. The frozen patches were then thawed, and each of the samples was mechanically tested. Upon thawing it was observed that the water content of the frozen patches appeared to be lower than that of the patches stored at room temperature. The results of the mechanical tests are shown in FIG. 4B. The frozen patches were stronger with slightly lower extension when compared to the control. It was determined that freezing and thawing the patch significantly enhances strength but not necessarily flexibility.

Figure 4C:
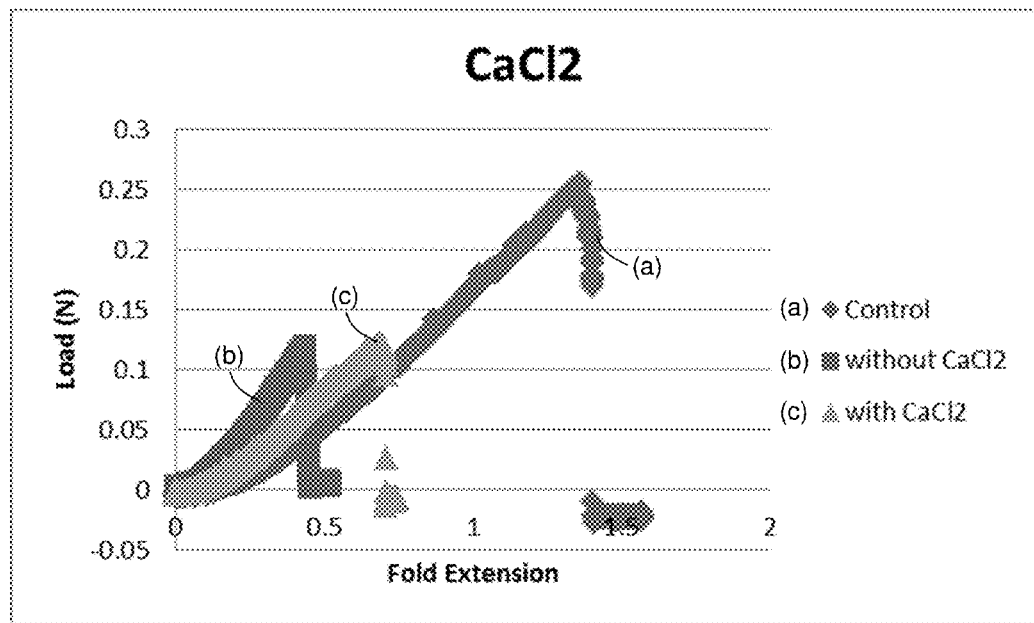

In another set of experiments, the effects of including $CaCl_2$ in the patch formulation were investigated. One set of patches was fabricated using the $CaCl_2$ described in the procedures outlined above, while another set was made without including the $CaCl_2$. The plasma and thrombin concentrations were identical, as were the storage and sterilization (30 kGy) conditions. FIG. 4C includes a plot of the stress-strain curves of the tested patches. From these results, it was determined that the inclusion of $CaCl_2$ enhanced flexibility, but not necessarily strength.

Figure 4D:
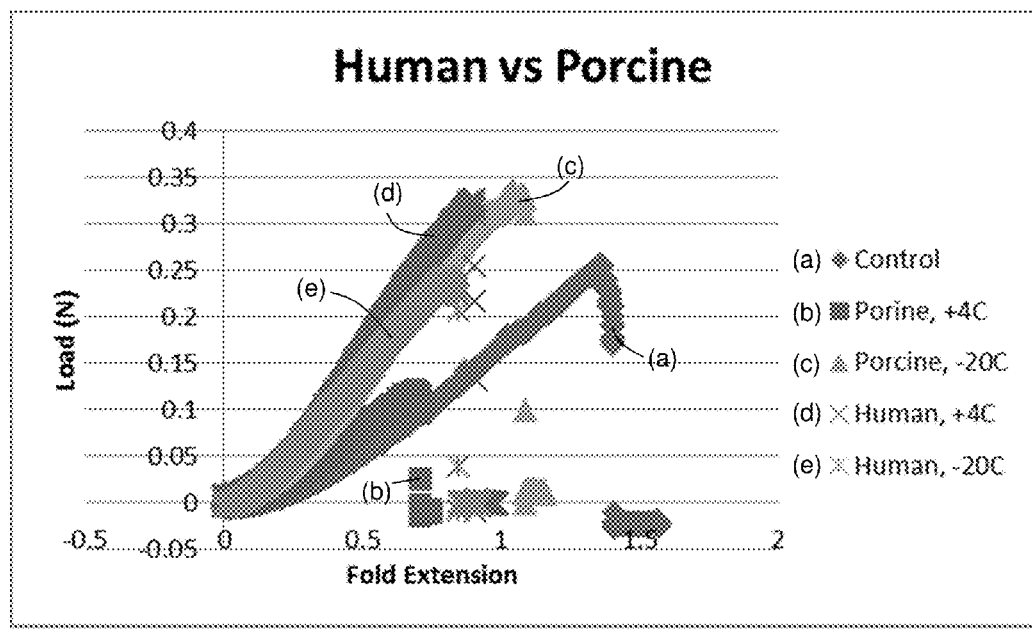
Figure 4E:
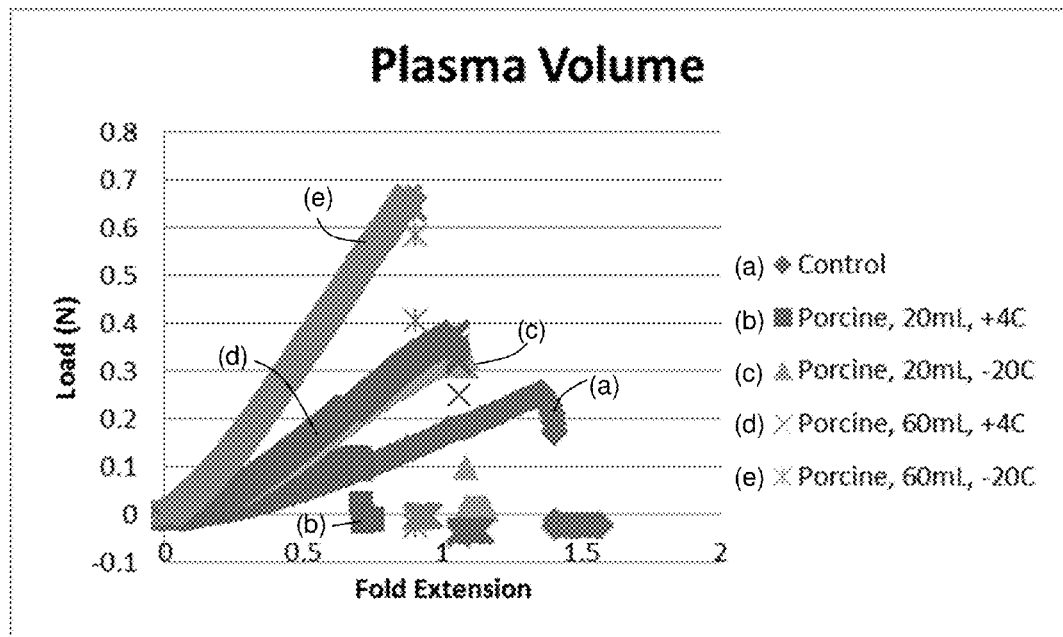

The impact of plasma type was also studied. One set of patches was fabricated using porcine plasma, while another set of patches was made using human plasma. Human plasma (fresh frozen plasma) was sourced from the American Red Cross and Seroplex were tested, and each patch was made from plasma from a single donor. The porcine plasma was pooled from four different pigs. Sodium citrate was added to the porcine plasma to form a mixture containing 3.8 wt % sodium citrate. Both plasma types were processed identically to remove cells. FIG. 4D includes the results of mechanical testing performed on these sets of patches. One set of patches was stored at 4° C. (labeled "+4 C" in FIG. 4D) while another set of patches was stored at −20° C. (labeled "−20 C" in FIG. 4D). From these results, it was determined that patches made using human plasma were at least as strong and flexible as those made from porcine plasma, if not moreso.

In another set of experiments, the effect of varying the volume of the porcine plasma used to make the patches was investigated. One set of patches was made using 20 mL of porcine plasma while another set of patches was made using 60 mL of porcine plasma. The ratios of $CaCl_2$ and thrombin in the formulations were kept identical (600 microliters of 2M $CaCl_2$ and 600 microliters of 3000 U/mL thrombin for the 60 mL patches). The results of the mechanical testing performed on these patches are summarized in FIG. 4E. From these results, it was determined that using larger volumes of plasma tends to produce stronger and more flexible patches.

Figure 4F:
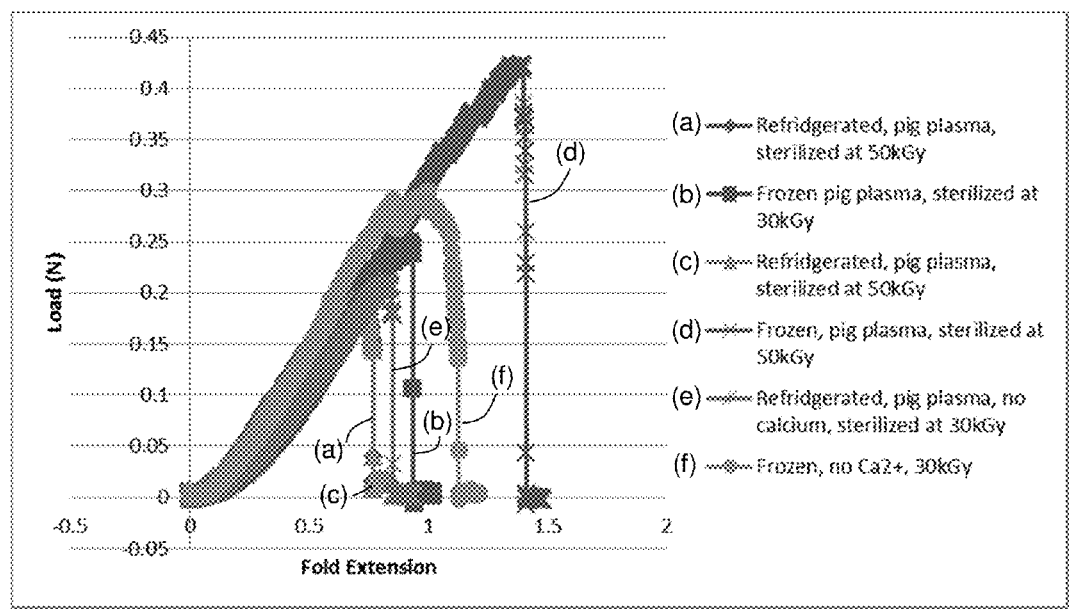

In another set of tests, the effect of aging the patches was investigated. One set of patches was aged for 30 days in a refrigerated environment at 4° C. Another set of patches was frozen for 30 days at −20° C. A final set of patches was stored for 7 days at room temperature. The results of mechanical testing are shown in FIG. 4F.

Example 6

This example describes the antimicrobial performance of a zinc oxide-containing primer layer. The antimicrobial activity of the primer was evaluated using 5% sheep blood agar plates. A first pair of plates was inoculated with a clinical isolate of 1000 CFU/mL of *Bacillus cereus*. A second pair of plates was inoculated with a clinical isolate of 1000 CFU/mL of *Pseudomonas aeruginosa*. For each plate pair, one plate was left alone as a "Control" plate, and a primer material comprising a zinc oxide eugenol mixture was applied to the second plate.

After 24 hours, bacterial counts were performed on the plates. After the 24-hour growth period, the "Control" plate inoculated with *Bacillus cereus* grew to over 1×10e5 CFU/mL. No growth was observed for the plate inoculated with *Bacillus Cerus* to which the primer was applied. The "Control" plate inoculated with *Pseudomonas aeruginosa* grew to 1×10e3 CFU/mL, whereas substantially no growth was observed on the plate inoculated with *Psudomonas aeruginosa* to which the primer was applied.

Example 7

This example describes the use of a patch with primer on both sides to approximate two tissue layers and to close potential space where exudate, transudate, blood or lymphatic fluid could accumulate reducing or obviating the need for post-surgical percutaneous wound drainage. In a porcine model, skin flaps were created using a Z-plasty technique and a U-shaped flap technique. The skin flaps were elevated by sharp dissection of underlying subcutaneous soft tissue remaining attached at the base. A patch with primer on both sides (using the patch and primer formulations described in Example 3) was positioned on the dissection bed and the flap lowered onto the exposed primer-coated patch surface. The skin was held in place for 60 seconds and firm adherence of the tissue flap was demonstrated immediately and confirmed on subsequent evaluation several hours later.

Example 8

This example describes experiments in which a tissue patch was used to seal bone tissue. A lateral approach to the porcine stifle joint was created. The joint capsule was incised, and the patella was reflected medially off the trochlear notch on the distal femur. An oscillating bone saw was used to remove the cartilage and underlying bone from both the medial and lateral trochlea and patches were applied to both bleeding bone defects. A tissue patch with primer on both sides was applied to the resulting cavity. Pressure was applied for 60 seconds and hemostasis demonstrated immediately which persisted several hours later.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively.

What is claimed is:

1. A patch, comprising:
a primer region comprising a water-activated polymeric adhesive; and
an unsupported solid matrix comprising fibrin positioned over at least a portion of the primer region, wherein:
the unsupported solid matrix has a Young's modulus of about 10 GPa or less after sterilization using gamma radiation at an intensity of 30 kGy, and
the patch is configured for application to a tissue surface.

2. A patch, comprising:
a primer region comprising a water-activated polymeric adhesive; and
an unsupported solid matrix comprising fibrin positioned over at least a portion of the primer region, wherein:
the fibrin within the unsupported solid matrix is cross-linked to a degree such that, after submerging the unsupported solid matrix in a 6M aqueous solution of urea at 25° C., the unsupported solid matrix retains its structural integrity over a period of at least about 2 hours, and
the patch is configured for application to a tissue surface.

3. The patch of claim 1, wherein the water-activated polymeric adhesive comprises a co-polymer of a vinyl ether and maleic anhydride.

4. The patch of claim 3, wherein the vinyl ether comprises an alkyl vinyl ether.

5. The patch of claim 4, wherein the alkyl group in the alkyl vinyl ether comprises from 1 to 18 carbons.

6. The patch of claim 4, wherein the alkyl vinyl ether comprises methylvinyl ether.

7. The patch of claim 3, wherein the vinyl ether comprises a divinyl ether.

8. The patch of claim 1, wherein the matrix optionally comprises fibrinogen, and wherein the total of fibrin and fibrinogen within the matrix is at least about 10 grams per liter of the matrix.

9. The patch of claim 1, wherein the matrix optionally comprises fibrinogen, and wherein the total of fibrin and fibrinogen within the matrix is between about 10 grams per liter and about 150 grams per liter of the matrix.

10. The patch of claim 1, wherein a concentration of the fibrin within the matrix is at least about 10 grams per liter of the matrix.

11. The patch of claim 1, wherein the patch comprises thrombin within the primer region.

12. The patch of claim 1, wherein the water-activated polymeric adhesive is present within the primer region in an amount of from about 5 wt % to about 50 wt %.

13. The patch of claim 1, wherein the matrix optionally comprises fibrinogen, and wherein the weight ratio of fibrin to fibrinogen within the matrix is at least about 5:1.

14. The patch of claim 1, wherein the water-activated polymeric adhesive comprises one or more polymers of acrylic acid.

15. The patch of claim 14, wherein the one or more polymers of acrylic acid are cross-linked with a polyalkenyl ether and/or a divinyl alcohol.

16. The patch of claim 15, wherein the one or more polymers of acrylic acid are cross-linked with a polyalkenyl ether.

17. The patch of claim 15, wherein the one or more polymers of acrylic acid are cross-linked with a divinyl alcohol.

18. The patch of claim 1, wherein the unsupported solid matrix has an aspect ratio of at least about 5:1.

19. The patch of claim 1, wherein the unsupported solid matrix has an average thickness of between about 500 microns and about 1 cm.

20. The patch of claim 1, wherein the unsupported solid matrix has at least one cross-sectional dimension of at least about 1 cm.

21. The patch of claim 1, wherein the patch is sterile.

22. The patch of claim 2, wherein the water-activated polymeric adhesive comprises a co-polymer of a vinyl ether and maleic anhydride.

23. The patch of claim 22, wherein the vinyl ether comprises an alkyl vinyl ether.

24. The patch of claim 23, wherein the alkyl group in the alkyl vinyl ether comprises from 1 to 18 carbons.

25. The patch of claim 23, wherein the alkyl vinyl ether comprises methylvinyl ether.

26. The patch of claim 22, wherein the vinyl ether comprises a divinyl ether.

27. The patch of claim 2, wherein the matrix optionally comprises fibrinogen, and wherein the total of fibrin and fibrinogen within the matrix is at least about 10 grams per liter of the matrix.

28. The patch of claim 2, wherein the matrix optionally comprises fibrinogen, and wherein the total of fibrin and fibrinogen within the matrix is between about 10 grams per liter and about 150 grams per liter of the matrix.

29. The patch of claim 2, wherein the concentration of fibrin within the matrix is at least about 10 grams per liter of the matrix.

30. The patch of claim 2, wherein the patch comprises thrombin within the primer region.

31. The patch of claim 2, wherein the water-activated polymeric adhesive is present within the primer region in an amount of from about 5 wt % to about 50 wt %.

32. The patch of claim 2, wherein the matrix optionally comprises fibrinogen, and wherein the weight ratio of fibrin to fibrinogen within the matrix is at least about 5:1.

33. The patch of claim 2, wherein the water-activated polymeric adhesive comprises one or more polymers of acrylic acid.

34. The patch of claim 33, wherein the one or more polymers of acrylic acid are cross-linked with a polyalkenyl ether and/or a divinyl alcohol.

35. The patch of claim 34, wherein the one or more polymers of acrylic acid are cross-linked with a polyalkenyl ether.

36. The patch of claim 34, wherein the one or more polymers of acrylic acid are cross-linked with a divinyl alcohol.

37. The patch of claim 2, wherein the unsupported solid matrix has an aspect ratio of at least about 5:1.

38. The patch of claim 2, wherein the unsupported solid matrix has an average thickness of between about 500 microns and about 1 cm.

39. The patch of claim 2, wherein the unsupported solid matrix has at least one cross-sectional dimension of at least about 1 cm.

40. The patch of claim 2, wherein the patch is sterile.

41. The patch of claim 2, wherein the fibrin within the unsupported solid matrix is cross-linked to a degree such that, after submerging the unsupported solid matrix in an 8M aqueous solution of urea at 25° C., the unsupported solid matrix retains its structural integrity over a period of at least about 2 hours.

* * * * *